US010064742B2

(12) United States Patent
Taylor et al.

(10) Patent No.: US 10,064,742 B2
(45) Date of Patent: *Sep. 4, 2018

(54) CURVED SPACER AND INSERTER

(71) Applicant: EBI, LLC, Parsippany, NJ (US)

(72) Inventors: Daniel C. Taylor, Airmont, NY (US);
Anthony C. DeFalco, Andover, NJ (US)

(73) Assignee: Zimmer Biomet Spine, Inc.,
Westminster, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/487,791

(22) Filed: Apr. 14, 2017

(65) Prior Publication Data

US 2017/0216053 A1   Aug. 3, 2017

Related U.S. Application Data

(63) Continuation of application No. 13/278,738, filed on Oct. 21, 2011, now Pat. No. 9,622,879.

(51) Int. Cl.
*A61B 17/88* (2006.01)
*A61F 2/46* (2006.01)
(Continued)

(52) U.S. Cl.
CPC .......... *A61F 2/4611* (2013.01); *A61F 2/4465* (2013.01); *A61F 2002/3008* (2013.01);
(Continued)

(58) Field of Classification Search
CPC ............ A61F 2/4611; A61F 2002/4623; A61F 2002/4624; A61F 2002/4627; A61F 2002/4629
(Continued)

(56) References Cited

U.S. PATENT DOCUMENTS 6,174,311 B1   1/2001  Branch et al.
6,431,017 B1   8/2002  Robadey
(Continued)

OTHER PUBLICATIONS

"U.S. Appl. No. 13/278,738, Advisory Action dated Feb. 1, 2016", 3 pgs.

(Continued)

*Primary Examiner* — Tatiana Nobrega
*Assistant Examiner* — Marcela I Shirsat
(74) *Attorney, Agent, or Firm* — Schwegman Lundberg & Woessner, P.A.

(57) ABSTRACT

The present teachings provide one or more surgical implements for repairing damaged tissue, such as in the case of a spinal fixation procedure. A cross connector system for use during a spinal fixation procedure is provided. The system includes at least one bridge defining a coupling bore and having a pair of downwardly extending arms for coupling to a first fastener. The system includes a contoured bar having a first end offset from a second end, and a bore having a central axis. The system includes an expansion ring received within the bore, and a locking device received through the expansion ring and the coupling bore. The locking device is operable in a first state in which the contoured bar is movable about the central axis of the bore and in a second state in which the contoured bar fixed relative to the central axis of the bore.

18 Claims, 25 Drawing Sheets

(51) Int. Cl.
*A61F 2/44* (2006.01)
*A61F 2/30* (2006.01)

(52) U.S. Cl.
CPC .............. *A61F 2002/30266* (2013.01); *A61F 2002/30364* (2013.01); *A61F 2002/30538* (2013.01); *A61F 2002/30632* (2013.01); *A61F 2002/30772* (2013.01); *A61F 2002/30777* (2013.01); *A61F 2002/30779* (2013.01); *A61F 2002/30797* (2013.01); *A61F 2002/30836* (2013.01); *A61F 2002/30841* (2013.01); *A61F 2002/30843* (2013.01); *A61F 2002/4475* (2013.01); *A61F 2002/4623* (2013.01); *A61F 2002/4624* (2013.01); *A61F 2002/4625* (2013.01); *A61F 2002/4627* (2013.01); *A61F 2002/4629* (2013.01); *A61F 2310/00023* (2013.01); *A61F 2310/00179* (2013.01)

(58) Field of Classification Search
USPC .......... 606/99, 86 a, 914, 90, 915, 900, 901, 606/100, 108, 167, 170, 185, 62–63, 232, 606/233; 623/22.12, 17.15, 17.16
See application file for complete search history.

(56) References Cited

U.S. PATENT DOCUMENTS

| | | | |
|---|---|---|---|
| 7,575,580 | B2 | 8/2009 | Lim et al. |
| 8,425,529 | B2 | 4/2013 | Milz et al. |
| 9,622,879 | B2 | 4/2017 | Taylor |
| 2003/0083747 | A1 | 5/2003 | Winterbottom et al. |
| 2003/0149438 | A1 | 8/2003 | Nichols et al. |
| 2007/0123907 | A1 | 5/2007 | Weber |
| 2007/0225726 | A1 | 9/2007 | Dye et al. |
| 2008/0045968 | A1 | 2/2008 | Yu et al. |
| 2008/0077153 | A1* | 3/2008 | Pernsteiner ........... A61F 2/4425 606/99 |
| 2008/0119935 | A1 | 5/2008 | Alvarez |
| 2010/0094422 | A1 | 4/2010 | Hansell et al. |
| 2013/0103102 | A1 | 4/2013 | Taylor et al. |

OTHER PUBLICATIONS

"U.S. Appl. No. 13/278,738, Examiner Interview Summary dated May 18, 2015", 3 pgs.
"U.S. Appl. No. 13/278,738, Examiner Interview Summary dated Oct. 24, 2014", 3 pgs.
"U.S. Appl. No. 13/278,738, Final Office Action dated Oct. 22, 2015", 17 pgs.
"U.S. Appl. No. 13/278,738, Non Final Office Action dated Feb. 12, 2015", 16 pgs.
"U.S. Appl. No. 13/278,738, Non Final Office Action dated May 4, 2016", 16 pgs.
"U.S. Appl. No. 13/278,738, Non Final Office Action dated Jul. 31, 2014", 17 pgs.
"U.S. Appl. No. 13/278,738, Notice of Allowance dated Dec. 16, 2016", 9 pgs.
"U.S. Appl. No. 13/278,738, Response filed Feb. 8, 2016 to Final Office Action dated Oct. 22, 2015", 12 pgs.
"U.S. Appl. No. 13/278,738, Response filed Apr. 2, 2014 to Restriction Requirement dated Feb. 25, 2014", 11 pgs.
"U.S. Appl. No. 13/278,738, Response filed Jul. 9, 2015 to Non Final Office Action dated Feb. 12, 2015", 12 pgs.
"U.S. Appl. No. 13/278,738, Response filed Sep. 6, 2016 to Non Final Office Action dated May 4, 2016", 12 pgs.
"U.S. Appl. No. 13/278,738, Response filed Oct. 21, 2014 to Non Final Office Action dated Jul. 31, 2014", 13 pgs.
"U.S. Appl. No. 13/278,738, Response filed Dec. 14, 2015 to Final Office Action dated Oct. 22, 2015", 12 pgs.
"U.S. Appl. No. 13/278,738, Restriction Requirement dated Feb. 25, 2014", 6 pgs.

* cited by examiner

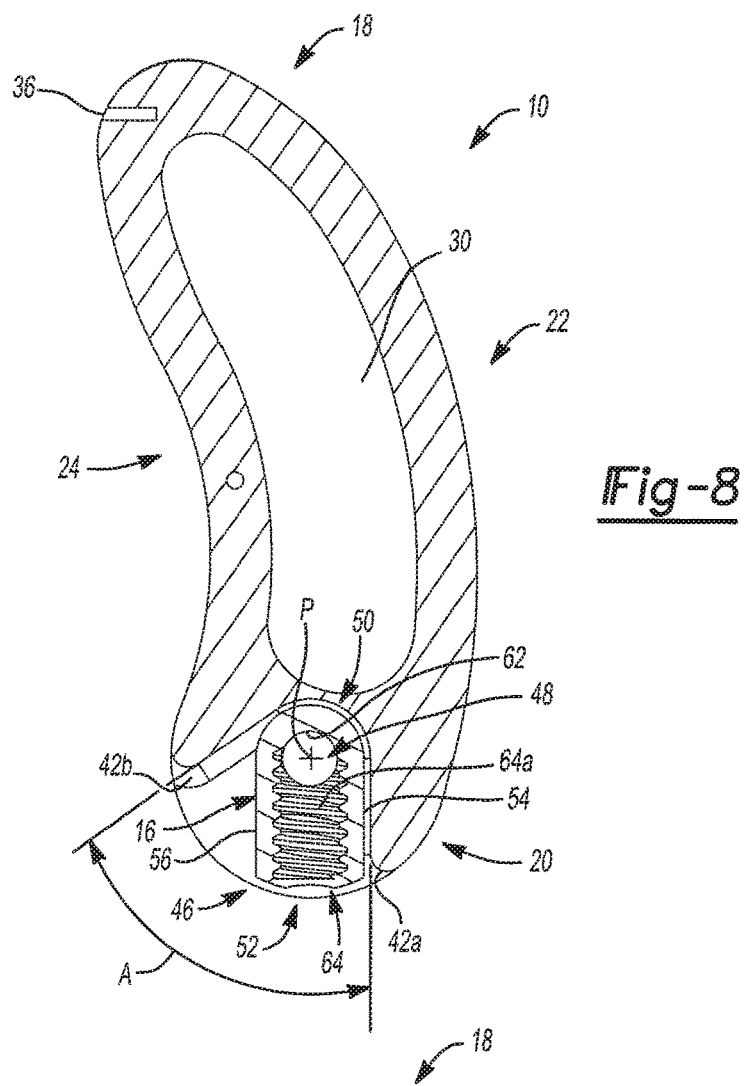
_Fig-8_
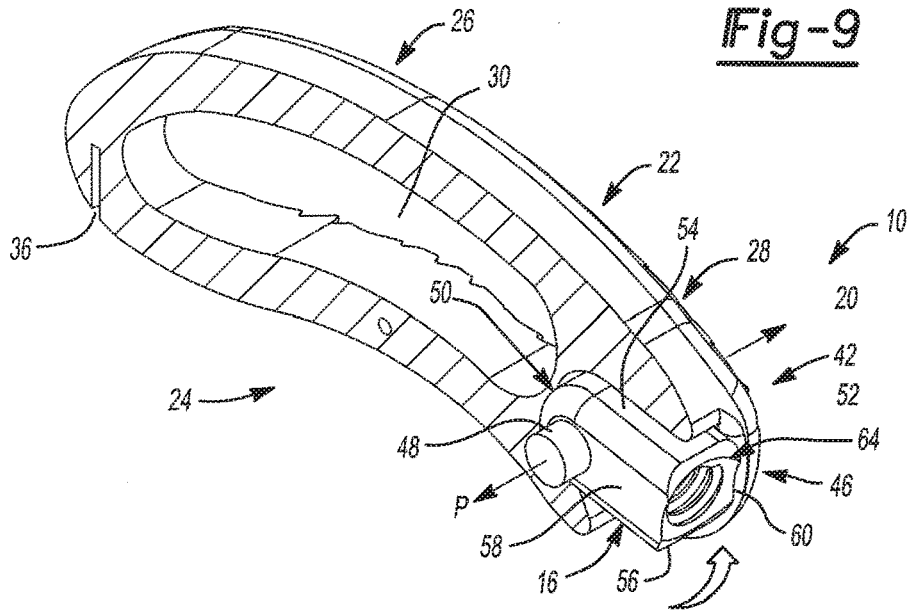
_Fig-9_

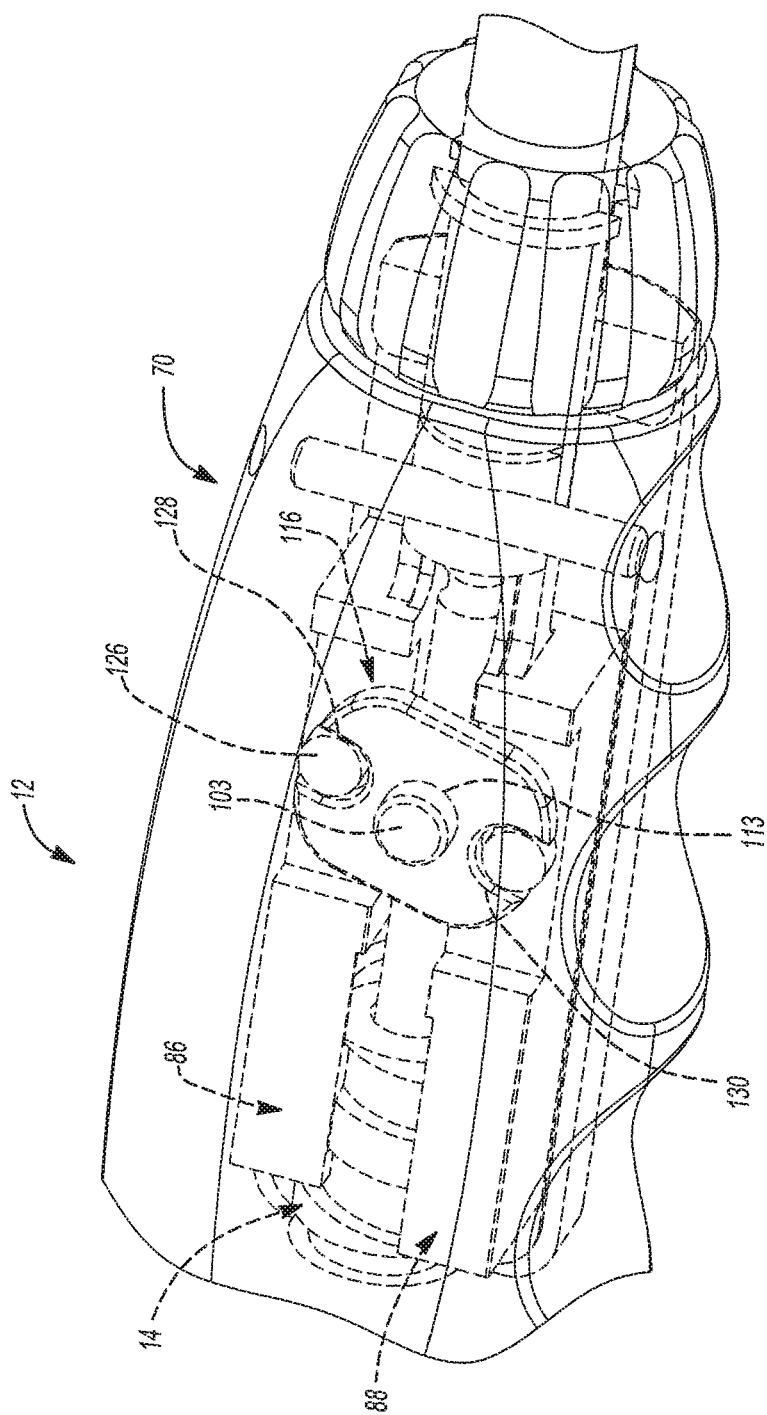

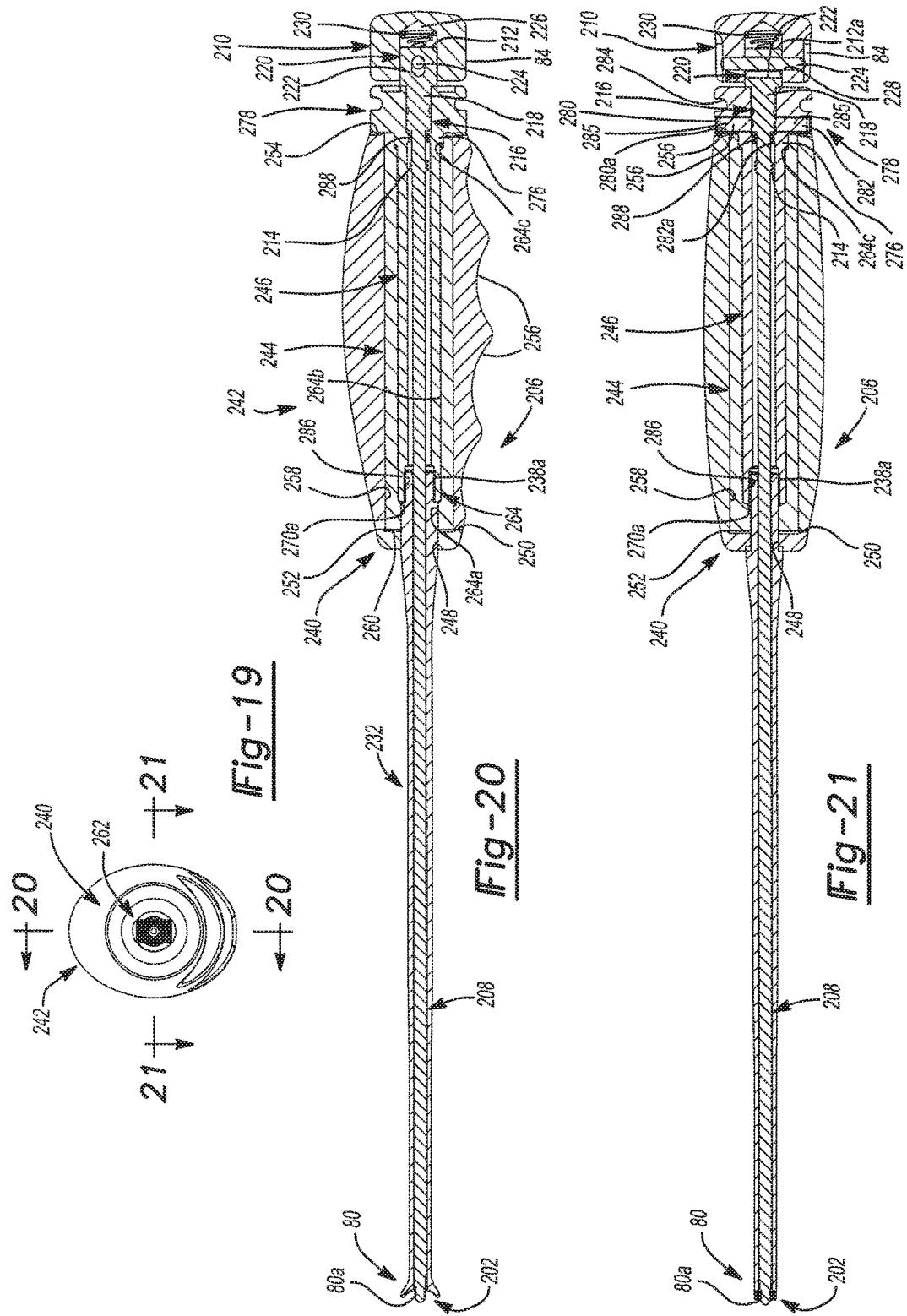

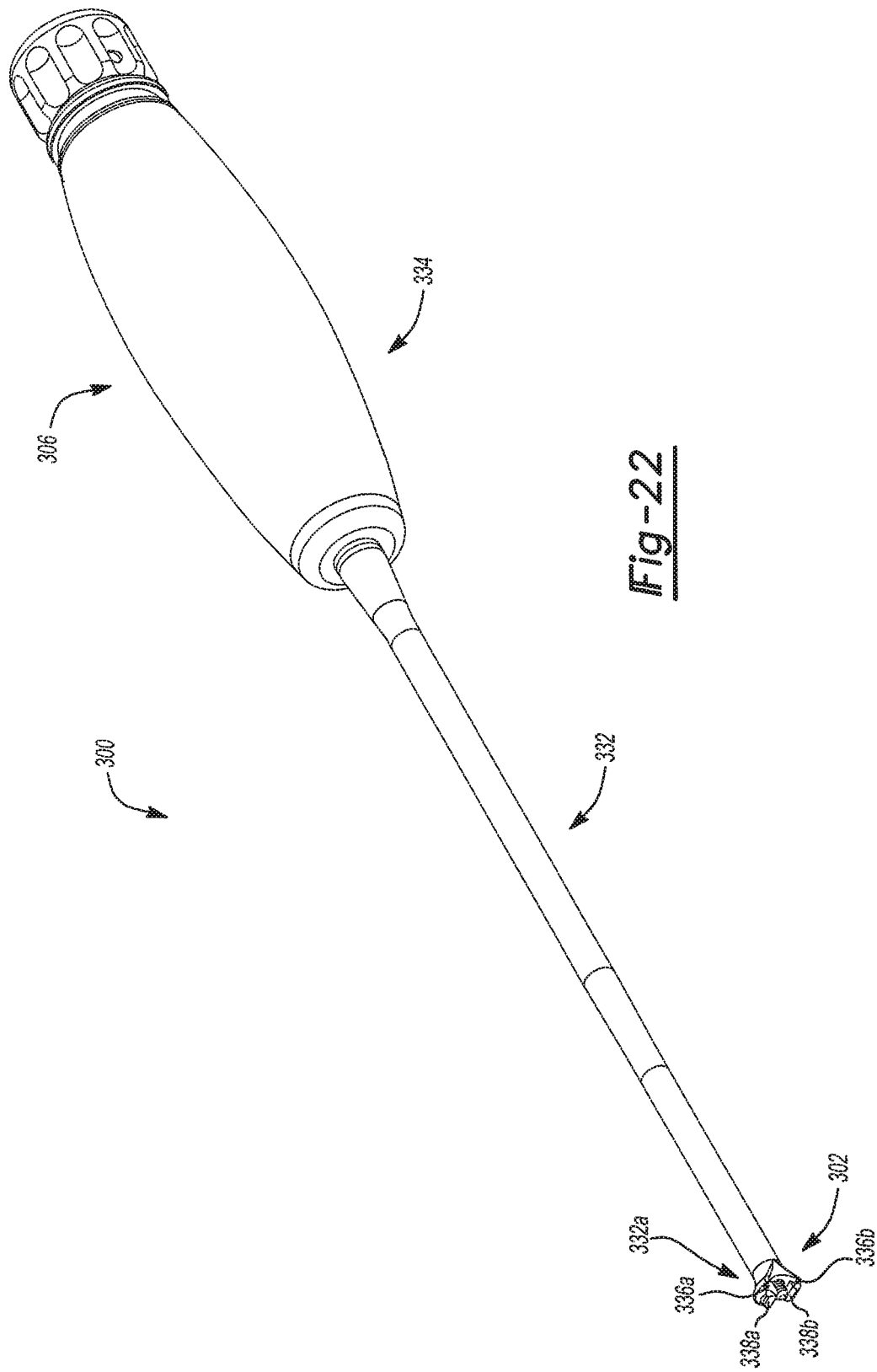

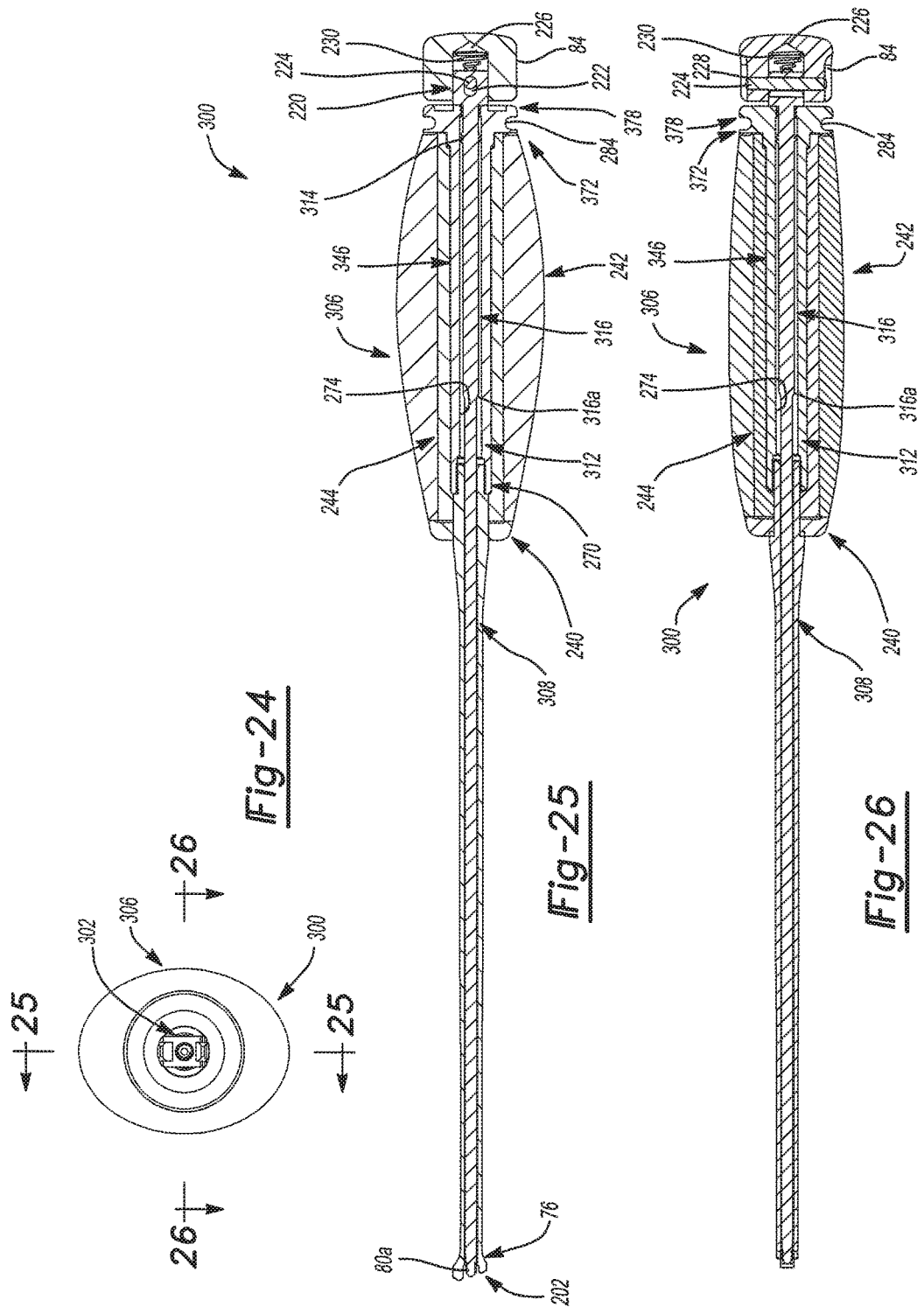

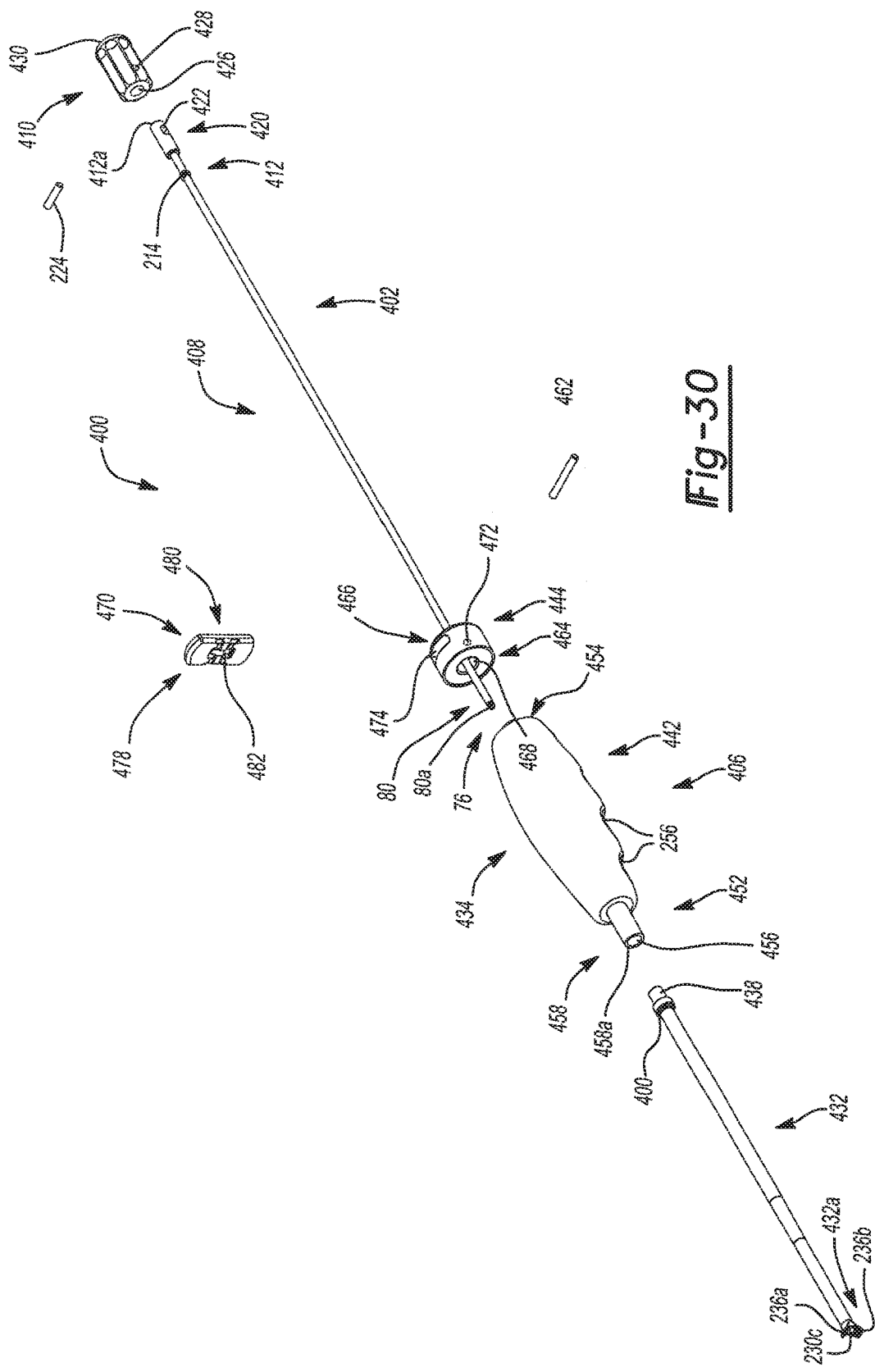

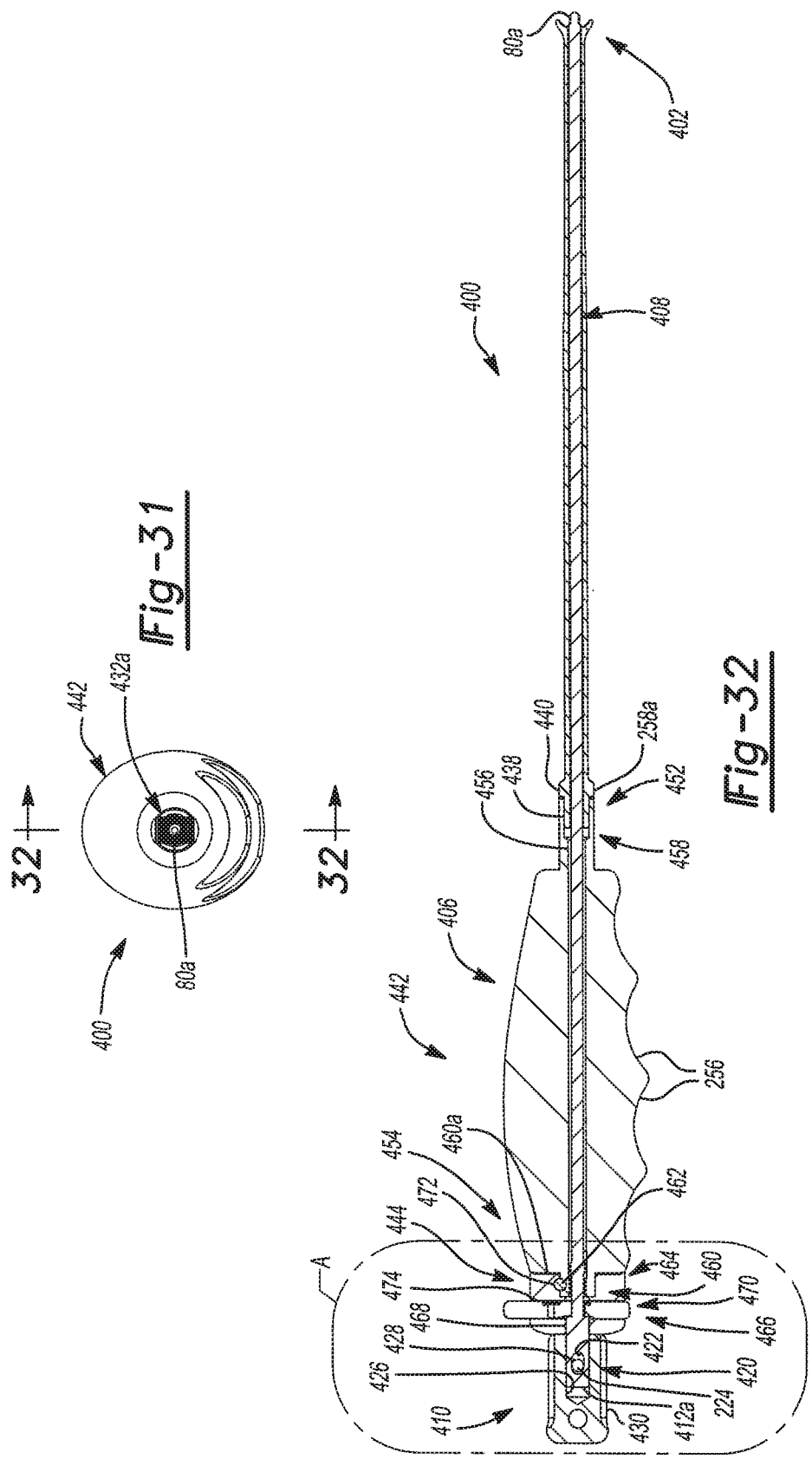

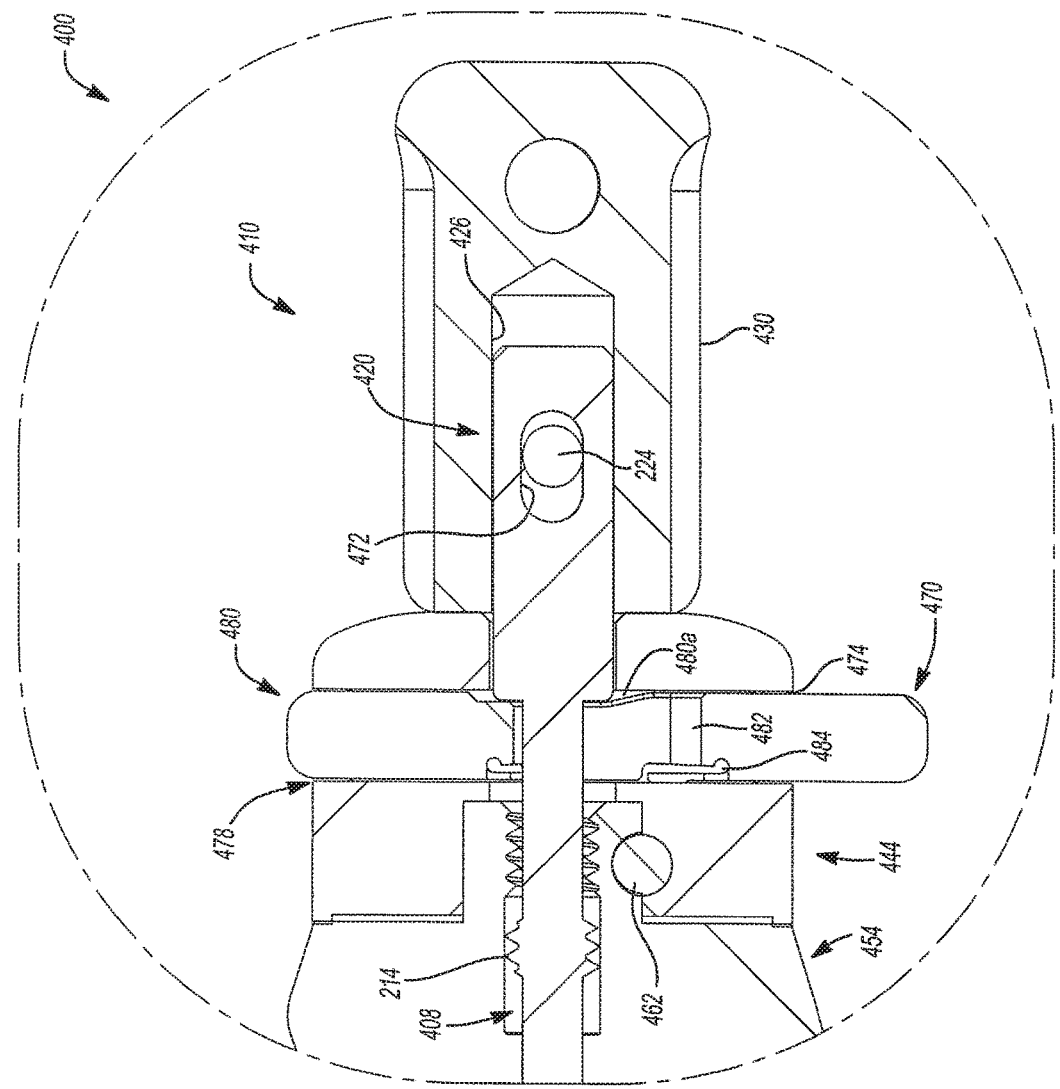

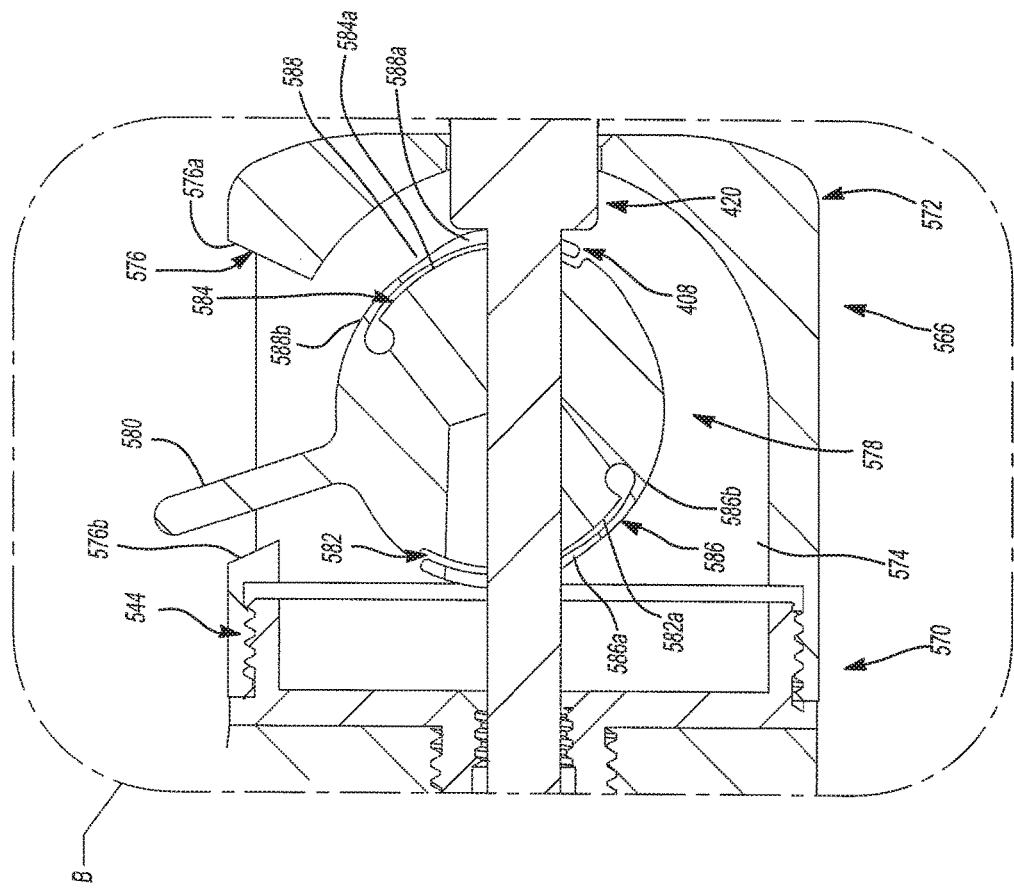

CURVED SPACER AND INSERTER

INTRODUCTION

In general, the human musculoskeletal system is composed of a variety of tissues including bone, ligaments, cartilage, muscle, and tendons. Tissue damage or deformity stemming from trauma, pathological degeneration, or congenital conditions often necessitates surgical intervention to restore function. Surgical intervention can include any surgical procedure that can restore function to the damaged tissue, which can require the use of one or more orthopedic prosthesis, such as orthopedic nails, screws, implants, etc., to restore function to the damaged tissue. In certain instances, such as in a spinal fusion procedure, it can be desirable to insert an implant into an intervertebral disc space to restore disc height and stabilize the vertebrae for long term spinal fusion.

The present teachings relate to a spinal implant and instrument system for use in a surgical procedure, such as a spinal fusion procedure, and more specifically relates to a curved spacer and an inserter for positioning the curved spacer within the anatomy.

SUMMARY

Provided is an instrument for inserting an interspinous spacer. The instrument can include an elongated body have a proximal end, a distal end and a first passage therebetween. The instrument can further include a handle at the proximal end of the body having a second passage therebetween. The instrument can include a rod received through the first passage and the second passage. The rod can be movable relative to the elongated body and the handle. The rod can have a distal end adapted to be coupled to the interspinous spacer. The instrument can include a first curved surface positioned adjacent to the distal end of the elongated body and adapted to contact the interspinous spacer. The instrument can also include a second curved surface positioned adjacent to the distal end of the elongated body opposite the first curved surface. The second curved surface can be adapted to contact the interspinous spacer.

Further provided is an instrument for inserting an interspinous spacer. The instrument can include an elongated body have a proximal end and a distal end, and a handle coupled to the proximal end of the body having a passage therebetween. The instrument can include a first arm movable relative to the elongated body, which can be received at least partially within the passage. The first arm can have a proximal end and a distal end. The distal end can be adapted to contact the interspinous spacer. The proximal end of the first arm can define at least one engagement feature. The instrument can include a second arm movable relative to the elongated body, which can be received at least partially within the passage. The second arm can be positioned relative to the first arm about the elongated body. The second arm can have a proximal end and a distal end. The distal end can be adapted to contact the interspinous spacer. The instrument can include a drive system received at least partially within the handle, which can interact with the first engagement member such that movement of the drive system moves the first arm reciprocally relative to the second arm.

Also provided is an instrument for inserting an interspinous spacer. The instrument can include an elongated body have a proximal end, a distal end and a first passage. The instrument can include a handle coupled to the proximal end of the body having a second passage therebetween. The instrument can also include a first arm slidable relative to the elongated body and the handle. The first arm can have a proximal end received within the second passage and a distal end adapted to contact the interspinous spacer. The distal end can be positioned along the elongated body. The proximal end of the first arm can define a plurality of threads and a link feature. The instrument can include a second arm slidable relative to the elongated body and the handle. The second arm can have a proximal end received within the second passage and a distal end adapted to contact the interspinous spacer. The distal end can be positioned along the elongated body. The second arm can be positioned opposite to the first arm. The proximal end of the second arm can have a link feature. The instrument can include a driver received within the second passage defining a plurality of threads threadably engagable with the plurality of threads of the first arm. The driver can be rotatable within the second passage to cause translation of the first arm relative to the elongated body and the handle. The instrument can include a pivoting link retained within the second passage and in communication with the link feature of the first arm and the link feature of the second arm so that the translation of the first arm causes reciprocal motion of the second arm.

Still yet also provided is an instrument for inserting an implant having a handle defining a bore longitudinally extending therethrough. A rod passes through the bore. The rod has a proximal end on a proximal side of the handle and a distal end on a distal side of the handle. The distal end is adapted to releasably engage the implant. A knob is carried at the proximal end of the rod for rotating the rod relative to the housing. The knob is coupled to the rod such that the knob is displaceable relative to the rod in a direction toward the distal end of the rod.

Further areas of applicability will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 8 is a cross-sectional view of the curved spacer of FIG. 1, taken along line 8-8 of FIG. 7;

FIG. 9 is a perspective, partially broken away view of the curved spacer of FIG. 1, illustrating an exemplary coupling portion of the curved spacer;

FIG. 12 is a cross-sectional view of the curved spacer and inserter of FIG. 1, taken along line 12-12 of FIG. 10;

FIG. 13 is a cross-sectional view of the curved spacer and inserter of FIG. 1, taken along line 13-13 of FIG. 10;

FIG. 14 is a schematic illustration of a portion of an exemplary drive system for use with the inserter of FIG. 1;

FIG. 19 is an end view of the inserter of FIG. 17;

FIG. 20 is a cross-sectional view of the curved spacer and inserter of FIG. 17, taken along line 20-20 of FIG. 19;

FIG. 21 is a cross-sectional view of the curved spacer and inserter of FIG. 17, taken along line 21-21 of FIG. 19;

FIG. 22 is perspective view of another exemplary inserter for use with the curved spacer according to the present teachings;

FIG. 24 is an end view of the inserter of FIG. 22;

FIG. 25 is a cross-sectional view of the curved spacer and inserter of FIG. 22, taken along line 25-25 of FIG. 24;

FIG. 26 is a cross-sectional view of the curved spacer and inserter of FIG. 22, taken along line 26-26 of FIG. 24;

FIG. 30 is an exploded view of the inserter of FIG. 29;

FIG. 31 is an end view of the inserter of FIG. 29;

FIG. 32 is a cross-sectional view of the curved spacer and inserter of FIG. 29, taken along line 32-32 of FIG. 31;

FIG. 33 is a detail cross-sectional view of a locking portion of the inserter of FIG. 29 taken from A of FIG. 32;

FIG. 39 is a detail cross-sectional view of a locking portion of the inserter of FIG. 35 taken from B of FIG. 38.

DESCRIPTION OF VARIOUS ASPECTS

Figure 1:
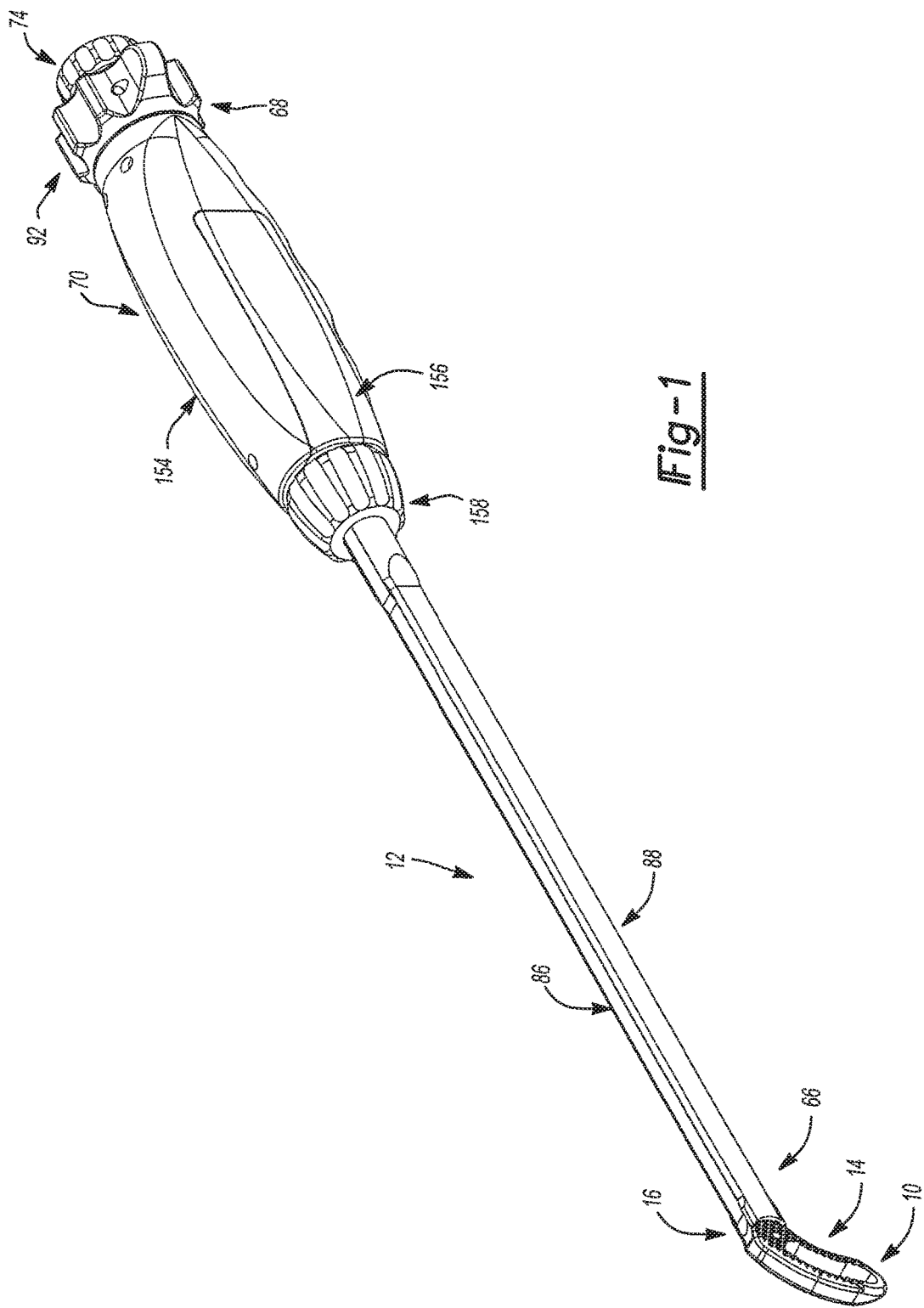
FIG. 1 is a perspective view of an exemplary curved spacer and inserter for use in a spinal fixation procedure according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a curved spacer and inserter for use in an anatomy to for a spinal fusion procedure, it will be understood that the curved spacer and inserter as described and claimed herein can be used in any appropriate surgical procedure, such as in a minimally invasive procedure. Therefore, it will be understood that the following discussions are not intended to limit the scope of the present teachings and claims herein.

Figure 2:
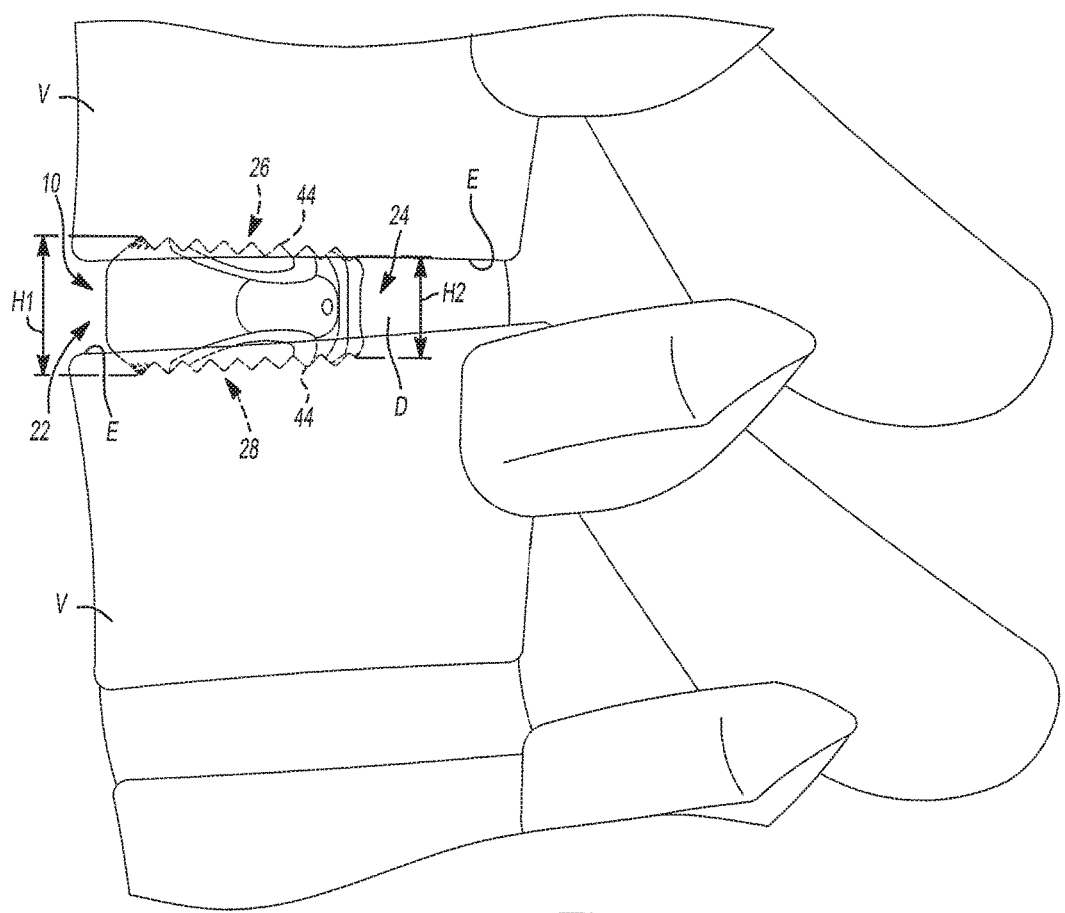
FIG. 2 is an environmental view of the curved spacer of FIG. 1 positioned between endplates of adjacent vertebral bodies according to the present teachings.
Figure 3:
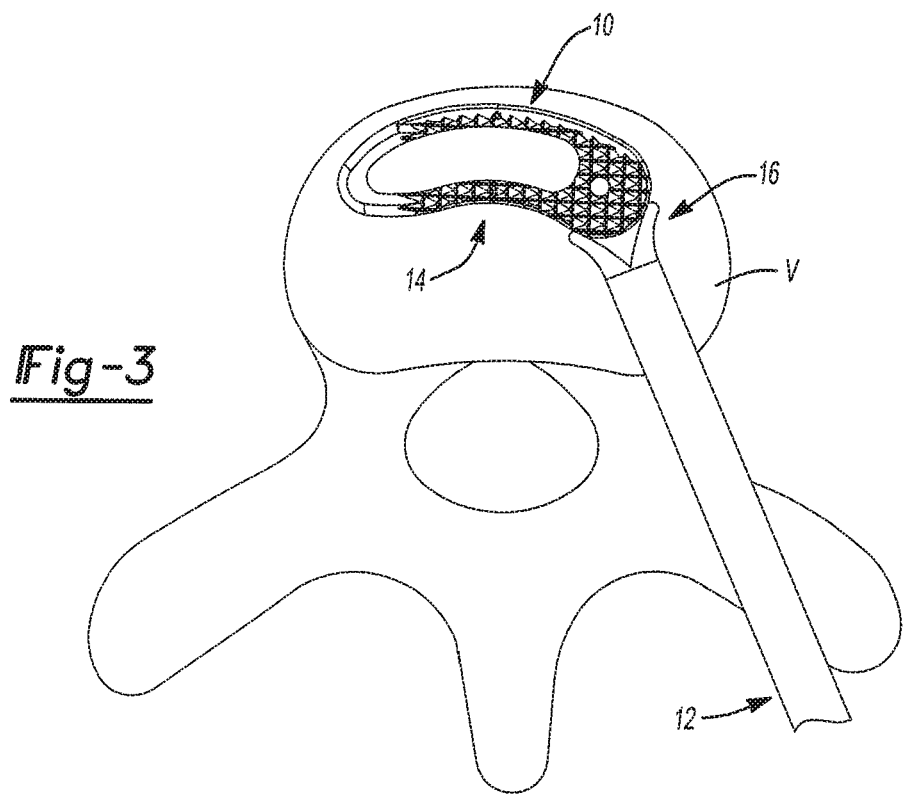
FIG. 3 is a schematic environmental illustration of the inserter of FIG. 1 positioning the curved spacer within the anatomy.

With reference to FIGS. 1-16, a curved spacer 10 and an exemplary inserter 12 is shown. The curved spacer 10 may be particularly adapted for spinal fusion procedures, such as a trans-foraminal intervertebral fusion procedure. Various aspects of the present teachings, however, may have application for other procedures. In certain applications, with reference to FIG. 2, the curved spacer 10 can be positioned within an intervertebral disc space D, between adjacent vertebral bodies V to restore disc height and stabilize the vertebrae for long-term spinal fusion. It should be noted that although a single curved spacer 10 will be described and illustrated herein as being positioned within an intervertebral disc space, multiple curved spacers 10 could be used in various locations along the spinal column depending upon the selected procedure. As will be discussed herein, the curved spacer 10 can be inserted into the anatomy via the inserter 12 (FIG. 3). The curved spacer 10 can include a main body 14 and a coupling portion 16.

Figure 4:
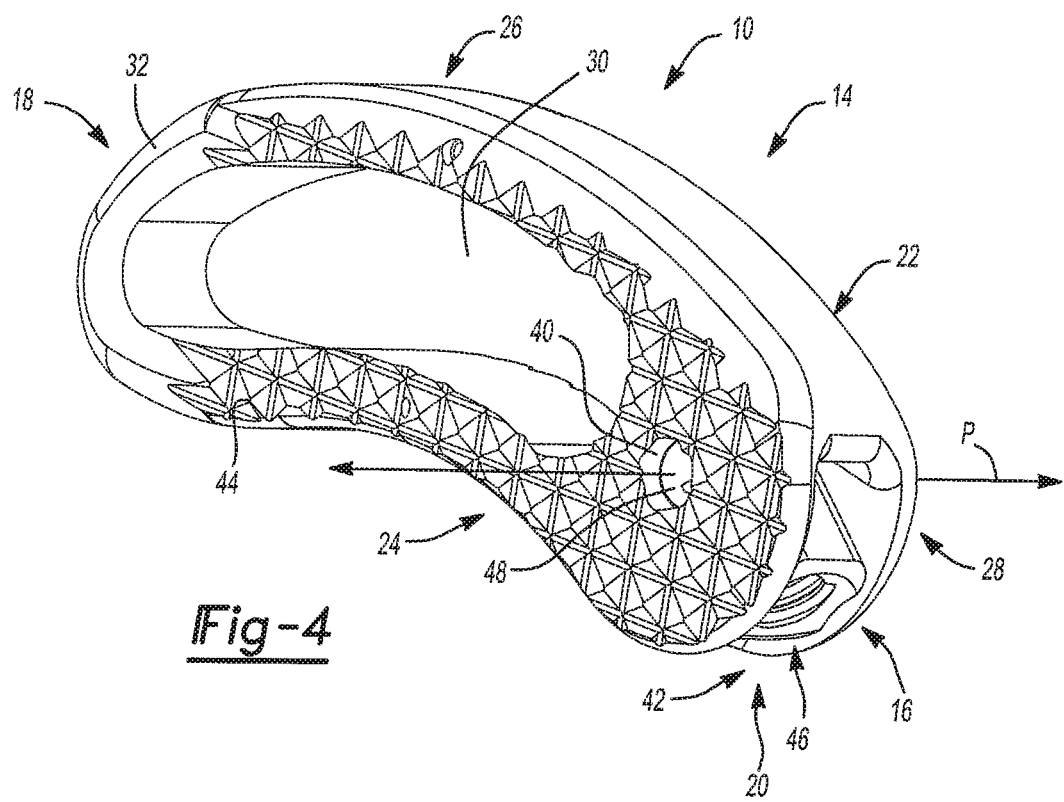
FIG. 4 is a perspective view of the curved spacer of FIG. 1.
Figure 5:
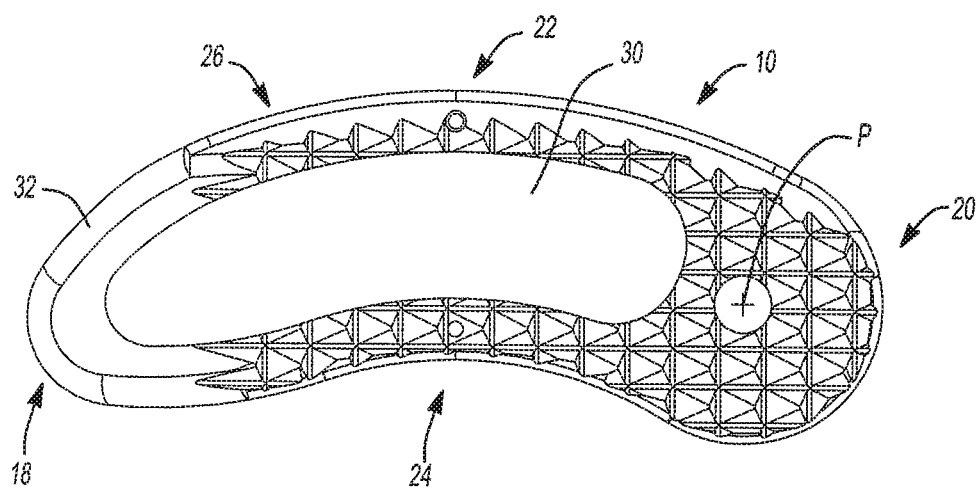
FIG. 5 is a top view of the curved spacer of FIG. 1.
Figure 6:
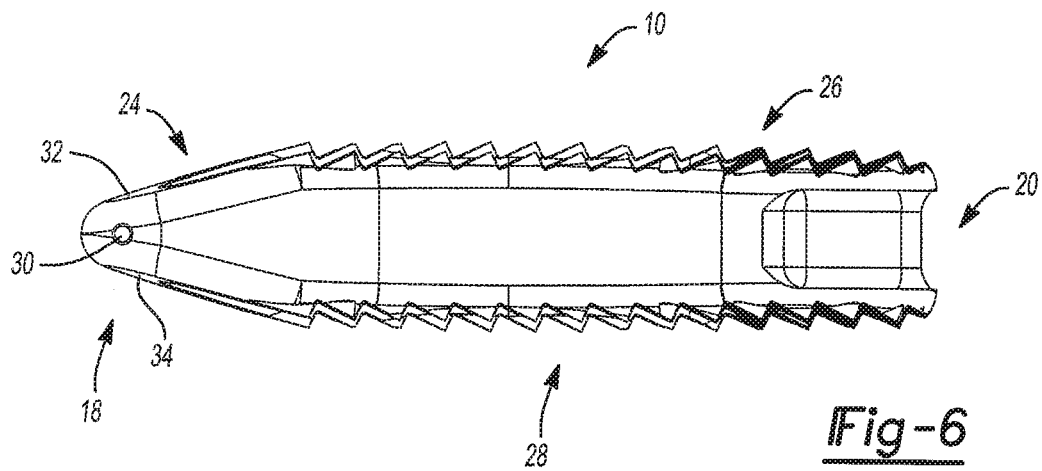
FIG. 6 is a side view of the curved spacer of FIG. 1.

The main body 14 of the curved spacer 10 can be shaped to conform to the anterior curve of the vertebral body V (FIG. 3). In one example, the main body 14 can have a kidney shape, however, the main body 14 could have any selected shape. The main body 14 can be comprised of a suitable biocompatible material, such as a biocompatible metal, polymer or ceramic. For example, the main body 14 can be composed of polyether ether ketone (PEEK), but the main body 14 could also be formed of titanium. With reference to FIGS. 4-6, the main body 14 can include a first or distal end 18, a second or proximal end 20, a first side 22, a second side 24, a first or superior surface 26, a second or inferior surface 28 (FIG. 6) and a cavity 30.

Figure 7:
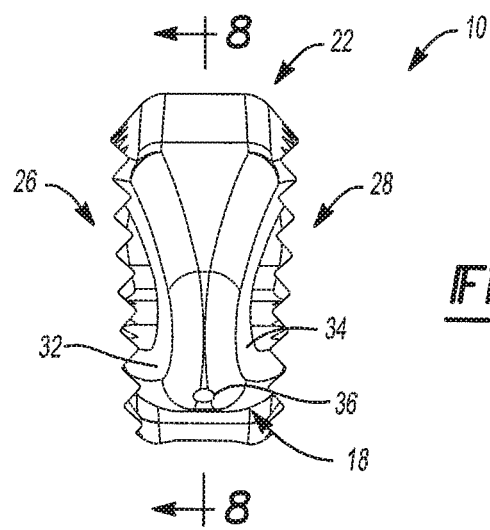
FIG. 7 is an end view of the curved spacer of FIG. 1.
Figure 10:
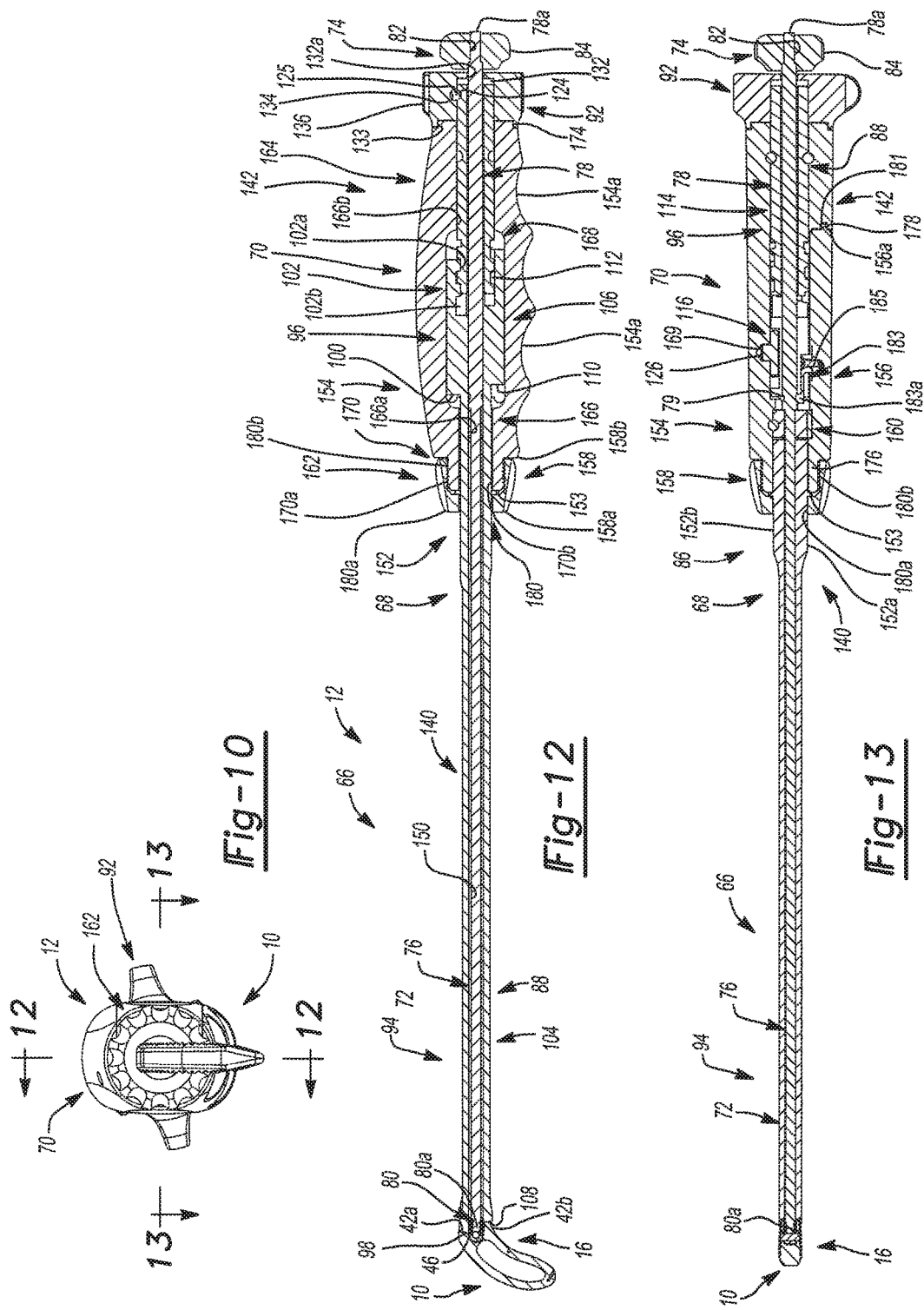
FIG. 10 is an end view of the curved spacer and inserter of FIG. 1.

With reference to FIGS. 6 and 7, the distal end 18 can include a first beveled surface 32 generally opposite a second beveled surface 34. The first beveled surface 32 and second beveled surface 34 can assist in distracting the adjacent vertebral bodies V during the insertion of the curved spacer 10, and can assist in navigating the curved spacer 10 through the anatomy. The distal end 18 can also include a recess 36. The recess 36 can receive at least one radiopaque marker 38. The at least one radiopaque marker 38 can enable an operator to determine the location of the distal end 18 using a suitable imaging device, such as a fluoroscope, etc.

With reference to FIG. 4, the proximal end 20 can be substantially opposite the distal end 18. The proximal end 20 can be generally curved about a pivot axis P. The proximal end 20 can include a coupling bore 40 and a pocket 42. The coupling bore 40 can receive part of the coupling portion 16 to couple the coupling portion 16 to the main body 14. The coupling bore 40 can be defined about the pivot axis P, from the superior surface 26 to the inferior surface 28.

With reference to FIGS. 8 and 9, the pocket 42 can receive part of the coupling portion 16 to couple the coupling portion 16 to the main body 14. The pocket 42 can be defined between the superior surface 26 and the inferior surface 28 (FIG. 9). The pocket 42 can be formed to be in communication with a portion of the coupling bore 40. The pocket 42 can enable the coupling portion 16 to move or pivot about the pivot axis P a selected amount of degrees. In one example, with reference to FIG. 8, the pocket 42 can be defined along an arc A of about 35 degrees to about 75 degrees. Thus, the coupling portion 16 can move or pivot about the pivot axis P from about 35 degrees to about 75 degrees. The pocket 42 can include a first rounded edge 42a and a second rounded edge 42b. The first rounded edge 42a and the second rounded edge 42b can cooperate with the inserter 12 to enable the curved spacer 10 to move relative to the inserter 12.

With reference to FIG. 4, the first side 22 can be generally opposite the second side 24, and can be defined between the distal end 18 and the proximal end 20. The first side 22 can be substantially arcuate, and in one example, can be generally concave. With reference to FIG. 2, the first side 22 can have a height H1, which can be less than a height H2 of the second side 24. The difference in the heights H1, H2 can enable the main body 14 to have a wedge-like shape. In one example, the height H2 can comprise a height of the curved spacer 10. The height H2 can vary so that the curved spacer 10 can be provided with various heights. In one example, the height H2 can range from about 20 millimeters (mm) to about 50 millimeters (mm). The second side 24 can be defined between the distal end 18 and the proximal end 20. The second side 24 can have the height H2, and can be substantially arcuate in shape. In one example, the second side 24 can be generally concave.

The superior surface 26 can be defined between the distal end 18 and the proximal end 20, and can be opposite the inferior surface 28. The superior surface 26 can contact an endplate E of an adjacent vertebral body V. The superior surface 26 can include a texture 44. The texture 44 can resist expulsion of the main body 14 from between adjacent vertebral bodies V and can resist motion of the main body 14 relative to the adjacent vertebral bodies. In one example, the texture 44 can comprise a plurality of teeth, which can bite into the adjacent vertebral bodies. It should be noted, however, that any suitable texture could be employed, such as one or more protrusions, grooves, etc. Further, a suitable coating could be applied as the texture 44. The inferior surface 28 can be defined between the distal end 18 and the proximal end 20. The inferior surface 28 can contact an endplate E of an adjacent vertebral body V. The inferior surface 28 can include the texture 44. It should be noted that although not illustrated herein, the texture 44 on the inferior surface 28 could be different than the texture 44 on the superior surface 26, if desired.

With reference to FIG. 4, the cavity 30 can be defined through the main body 14 from the superior surface 26 to the inferior surface 28. Generally, the cavity 30 can be formed between the first side 22 and the second side 24, and between the distal end 18 and the proximal end 20. The cavity 30 can facilitate bone in-growth, and can be used to hold graft material.

The coupling portion 16 can include a coupling body 46 and a pin 48. The coupling portion 16 can be composed from any suitable biocompatible material, such as biocompatible metal, polymer or ceramic. In one example, the coupling portion 16 can be comprised of titanium. The coupling body 46 can be sized to be received within and movable relative to the pocket 42. With reference to FIGS. 8 and 9, the coupling body 46 can include a first or distal end 50, a second or proximal end 52, a first side 54, a second side 56, a first or superior surface 58 (FIG. 9) and a second or inferior surface 60 (FIG. 9).

With reference to FIG. 8, the distal end 50 can be generally rounded to mate with the shape of the pocket 42. The distal end 50 can include a throughbore 62. The throughbore 62 can be defined from the superior surface 58 to the inferior surface 60. The throughbore 62 can receive the pin 48 to couple the coupling body 46 to the main body 14.

Referring to FIG. 9, the proximal end 52 can be substantially square or rectangular. With reference to FIG. 8, the proximal end 52 can include a counterbore 64. The counterbore 64 can be defined through the proximal end 52 through a portion of the throughbore 62 of the distal end 50. The counterbore 64 can be substantially perpendicular to the throughbore 62. The counterbore 64 can include a plurality of threads 64a. The plurality of threads 64a can enable the coupling portion 16 to be threadably engaged with the inserter 12, as will be discussed in greater detail herein.

With regard to FIG. 8, the first side 54 of the coupling body 46 can be opposite the second side 56. The first side 54 and second side 56 can each be substantially flat with rounded corners. The first side 54 and the second side 56 can contact a respective rounded edge 42a, 42b of the pocket 42 to limit the motion of the coupling portion 16 relative to the ruin body 14. The superior surface 58 can be opposite the inferior surface 60. With reference to FIG. 9, the superior surface 58 and inferior surface 60 can each be generally flat to support vertical compressive loads placed on the main body 14.

The pin 48 can be sized to be received through the coupling bore 40 and the throughbore 62 of the coupling body 46. Thus, the pin 48 can couple the coupling body 46 to the main body 14. The pin 48 can be generally cylindrical, and can be press-fit into the main body 14, if desired. The pin 48 can enable the coupling body 46 to move or pivot relative to the main body 14 about the pivot axis P.

With reference to FIG. 1, the inserter 12 can be used to navigate and position the curved spacer 10 within the anatomy. The inserter 12 can be composed of any biocompatible material, such as a biocompatible metal or polymer. In one example, the inserter 12 can comprise an active angle inserter, which can enable a user to select a desired angle for the curved spacer 10 relative to the inserter 12, as will be discussed. By allowing the user to select the angle for the curved spacer 10 relative to the inserter 12 throughout the procedure, the user can better navigate through the specific patient anatomy. The inserter 12 can comprise an attachment system 66, an active angle system 68 and a housing 70.

Figure 11:
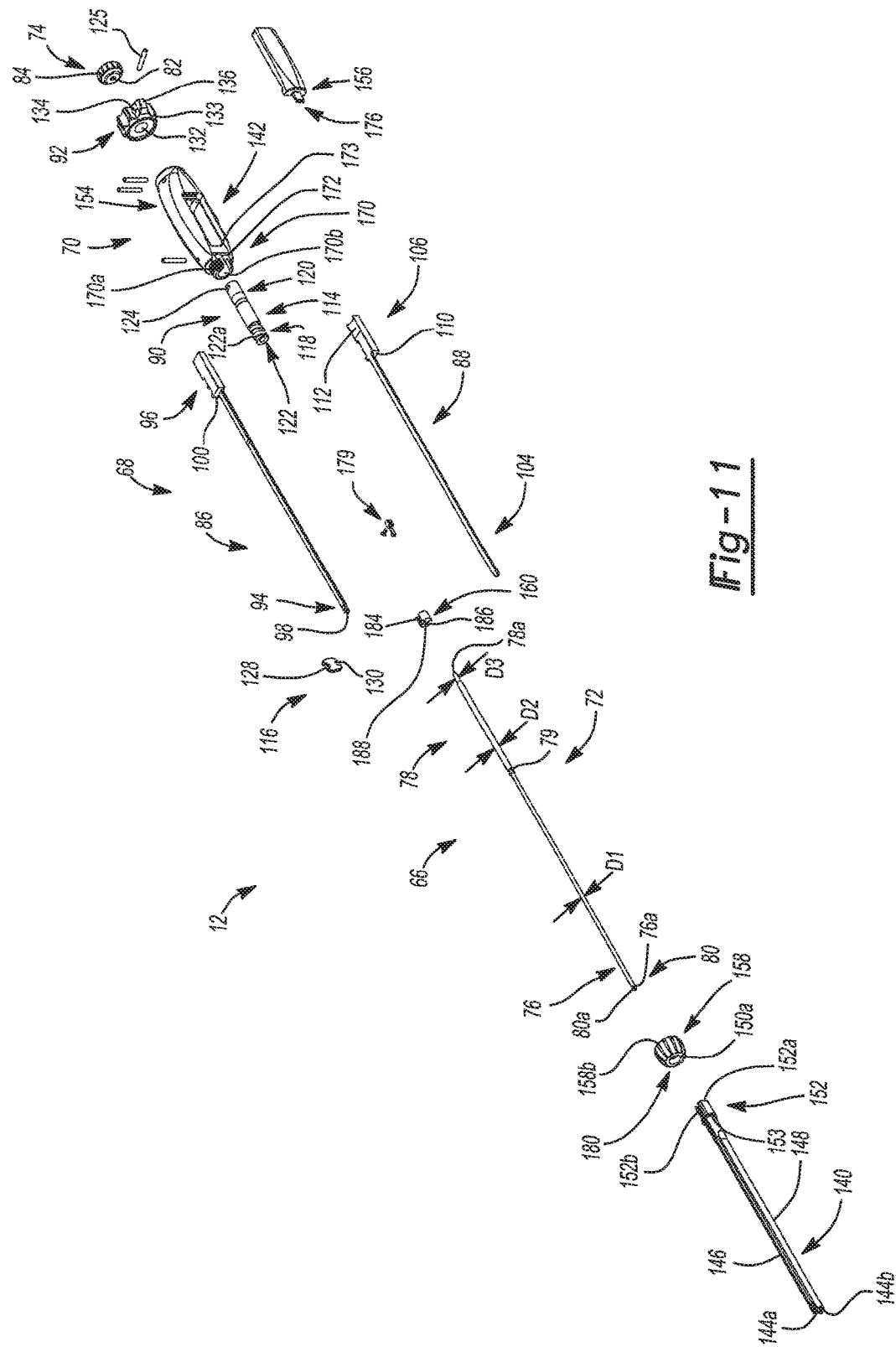
FIG. 11 is an exploded view of the inserter of FIG. 1.

With regard to FIG. 11, the attachment system 66 can couple the curved spacer 10 to the inserter 12. The attachment system 66 can include a rod 72 and a knob 74. The rod 72 can include a first or distal end 76 and a second or proximal end 78. The distal end 76 of the rod 72 can have a diameter D1, which can be less than a diameter D2 of the proximal end 78. The diameter D1 can be sized to enable the distal end 76 to be received within a portion of the housing 70. The distal end 76 can include a threaded portion 80. The threaded portion 80 can be formed at a distalmost end 76a. The threaded portion 80 can include a plurality of threads 80a, which can threadably engage a plurality of threads 46a of the coupling portion 16 to couple the curved spacer 10 to the inserter 12, as best shown in FIG. 12.

With reference back to FIG. 11, the proximal end 78 of the rod 72 can have the diameter D2, which can be sized to be received within another portion of the housing 70. The proximal end 78 can also include a diameter D3 at a proximalmost end 78a and a groove 79. The diameter D3 can be sized to enable the knob 74 to be press-fit onto the proximal end 78 of the rod 72. As will be discussed, the groove 79 can receive a portion of the housing 70 to assist in retaining the rod 72 within the housing 70.

With regard to FIGS. 12 and 13, the knob 74 can enable the user to rotate the rod 72 to couple or uncouple the curved spacer 10 from the inserter 12. The knob 74 can include a bore 82 and a graspable portion 84. The bore 82 can be coupled to the proximalmost end 78a of the rod 72, via a press-fit, for example. Alternatively, a mechanical fastener could be used to couple the knob 74 to the rod 72. The graspable portion 84 can provide a surface for the user to manipulate the knob 74. Generally, the knob 74 can be rotated in one direction to thread the threaded portion 80 into engagement with the coupling portion 16 of the curved spacer 10 to couple the curved spacer 10 to the inserter 12. The knob 74 can be rotated in an opposite direction to remove the threaded portion 80 from the coupling portion 16 to disengage the curved spacer 10 from the inserter 12.

Referring to FIG. 11, the active angle system 68 can enable the curved spacer 10 to be moved relative to the inserter 12. In one example, the active angle system 68 can include a first or active arm 86, a second or passive arm 88, a drive system 90 and an activation device 92. The active arm 86 and the passive arm 88 can operate in a reciprocal motion to change the angle of the inserter 12, as will be discussed herein.

The active arm 86 can have a first or distal end 94 and a second or proximal end 96. The distal end 94 can contact the curved spacer 10 and transmit axial load or impact from the user to the curved spacer. With reference to FIG. 12, the distal end 94 can define a curved surface 98. The curved surface 98 can remain in contact with the pocket 42 when the inserter 12 is coupled to the inserter 12. In one example, the curved surface 98 can move or slide along the first rounded edge 42a of the pocket 42 to assist in moving the curved spacer 10 relative to the inserter 12. The curved surface 98 can be generally smooth.

With reference to FIG. 11, the proximal end 96 can have a thickness, which can be greater than a thickness of the distal end 94. The increased thickness of the proximal end 96 can define a shoulder 100. With reference to FIG. 12, the shoulder 100 can contact a portion of the housing 70 to define a range of linear motion for the active arm 86. The proximal end 96 can also include a first driver engagement feature 102 and a linkage feature 103. The driver engagement feature 102 can cooperate with the drive system 90 to enable the active arm 86 to move relative to the housing 70. The driver engagement feature 102 can comprise a partial thread 102a and a cup-shaped recess 102b. The partial thread 102a can engage the drive system 90 to move the active arm 86 relative to the housing 70. The cup-shaped recess 102b can be configured to match a major diameter of the drive system 90 so that the proximal end 96 of the active arm 86 can be positioned around a portion of the drive system 90.

The linkage feature 103 can contact a portion of the drive system 90 to enable the transfer of motion between the active arm 86 and the passive arm 88. In one example, the linkage feature 103 can comprise a circular projection, which can extend outwardly from a surface of the active arm 86. The linkage feature 103 can be formed between the curved surface 98 and the proximal end 96.

With reference to FIG. 11, the passive arm 88 can have a first or distal end 104 and a second or proximal end 106. The passive arm 88 can move in a direction opposite the active arm 86 in a reciprocal motion. The passive arm 88 is generally not directly driven by the drive system 90. The distal end 104 can contact the curved spacer 10 and transmit axial load or impact from the user to the curved spacer. With reference to FIG. 12, the distal end 104 can define a curved surface 108. The curved surface 108 can be generally smooth, and can be substantially a mirror image of the curved surface 98. The curved surface 108 can remain in contact with the pocket 42 when the inserter 12 is coupled to the curved spacer 10. In one example, the curved surface 108 can move or slide along the second rounded edge 42b of the pocket 42 to assist in moving the curved spacer 10 relative to the inserter 12.

The proximal end 106 can have a thickness, which can be greater than a thickness of the distal end 104. The increased thickness of the proximal end 106 can define a shoulder 110. With reference to FIG. 12, the shoulder 110 can contact a portion of the housing 70 to define a range of linear motion for the passive arm 88. The proximal end 106 can also include a cut-out 112 and a linkage feature 113. The cut-out 112 can enable the passive arm 88 to be retained next to the drive system 90 without engaging the drive system 90. The cut-out 112 can comprise a smooth circular pocket, which can be sized to fit around a portion of the drive system 90.

The linkage feature 113 can contact a portion of the drive system 90 to enable the transfer of motion between the active arm 86 and the passive arm 88. In one example, the linkage feature 113 can comprise a circular projection, which can extend outwardly from a surface of the passive arm 88. The linkage feature 113 can be formed between the curved surface 108 and the proximal end 106.

With reference to FIG. 11, the drive system 90 can include a driver 114 and a pivoting link 116. The driver 114 can drive or move the active arm 86 relative to the housing 70. A pivoting link 116 can transmit the driving force of the active arm 86 to the passive arm 88 and can move the passive arm 88 in the opposite direction. The driver 114 can comprise a generally cylindrical shaft, with a first or distal end 118 and a second or proximal end 120. The driver 114 can be cannulated, to receive the rod 72 therethrough. The distal end 118 can include a driving feature 122. The driving feature 122 can include a plurality of threads 122a, which can engage the driver engagement feature 102 of the active arm 86.

Referring to FIG. 12, the proximal end 120 can include a coupling bore 124. The coupling bore 124 can receive a pin 125 to couple the activation device 92 to the driver 114. The movement or rotation of the activation device 92 can cause the movement or rotation of the driver 114. The movement or rotation of the driver 114 can cause the movement or translation of the active arm 86 relative to the housing 70.

The pivoting link 116 can transfer the motion of the active arm 86 to the passive arm 88, and can cause the passive arm 88 to move in a direction opposite the active arm 86. With reference to FIGS. 11, 13 and 14, the pivoting link 116 can include an annular projection 126 (FIG. 13), an active arm feature or notch 128 (FIGS. 11 and 14) and a passive arm feature or notch 130 (FIGS. 11 and 14). With regard to FIG. 13, the annular projection 126 can be received within a portion of the housing 70 to movably or pivotally couple the pivoting link 116 to the housing 70. Referring to FIG. 14, the active arm notch 128 can be shaped to receive the linkage feature 103 of the active arm 86 so as to be in communication with the linkage feature 103. In one example, the active arm notch 128 can be generally U-shaped to receive the annular projection of the linkage feature 103. The U-shape of the active arm notch 128 can enable the pivoting link 116 to move or pivot about the linkage feature 103 with the movement of the active arm 86 and can prevent the disengagement of the pivoting link 116 and the active arm 86.

The passive arm notch 130 can be positioned generally opposite the active arm notch 128. The passive arm notch 130 can be shaped to receive the linkage feature 113 of the passive arm 88. In one example, the passive arm notch 130 can be generally U-shaped to receive the annular projection of the linkage feature 113 so as to be in communication with the linkage feature 113. The U-shape of the passive arm notch 130 can enable the pivoting link 116 to move or pivot about the linkage feature 113 of the passive arm 88 to drive the passive arm 88 in a direction opposite the active arm 86 with the movement of the active arm 86. The U-shape can also prevent disengagement between the linkage feature 113 and the pivoting link 116.

With reference to FIGS. 11 and 12, the activation device 92 can be coupled to the driver 114. The activation device 92 can include a bore 132, a lip 133, a bore 134 and a graspable portion 136. The bore 132 can receive the proximal end 120 of the driver 114 and can enable the rod 72 to pass through the activation device 92 at a proximalmost end 132a (FIG. 12). The lip 133 can be formed annularly about the activation device 92, adjacent to the bore 132, and can facilitate coupling the activation device 92 to the housing 70. The bore 134 can be defined in a direction substantially perpendicular to the bore 132 and can be in communication with the bore 132.

Generally, with regard to FIG. 12, the distal end 118 of the driver 114 can be received within the bore 132 so that the coupling bore 124 is coaxially aligned with the bore 134. The pin 125 can pass through the bore 134 and the coupling bore 124 to couple the activation device 92 to the driver 114. The graspable portion 136 can provide a gripping surface for allowing the user to manipulate or rotate the activation device 92. The manipulation or rotation of the activation device 92 can move or rotate the driver 114, which in turn, can cause the active arm 86 to move or translate in a first direction and the passive arm 88 to move or translate in a second direction, opposite the first direction. The movement of the active arm 86 and the passive arm 88 can cause the curved spacer 10 to move relative to the inserter 12, as will be discussed herein.

With reference to FIG. 11, the housing 70 can enclose at least a portion of the attachment system 66 and the active angle system 68. The housing 70 can also provide a graspable portion for the user. The housing 70 can include a first or distal portion 140 and a second or proximal portion 142. The distal portion 140 of the housing 70 can be an elongated body. The distalmost end 140a of the distal portion 140 can include a first curved surface 144a opposite a second curved surface 144b. The first curved surface 144a and the second curved surface 144b can correspond to a shape of the proximal end 20 of the curved spacer 10. With regard to FIGS. 11 and 12, the distal portion 140 can include a first arm guide 146, a second arm guide 148, a passage or cannulated bore 150 (FIG. 12) and a coupling portion 152.

Referring to FIG. 12, the first arm guide 146 can be positioned opposite the second arm guide 148. The first arm guide 146 and the second arm guide 148 can slidably receive a respective one of the active arm 86 and passive arm 88. The cannulated bore 150 can be defined through the distal portion 140. The cannulated bore 150 can receive the proximal end 78 of the rod 72.

With reference to FIGS. 11 and 13, the coupling portion 152 can couple the distal portion 140 to the proximal portion 142. The coupling portion 152 can comprise a first flat portion 152a opposite a second flat portion 152b. The first flat portion 152a and the second flat portion 152b can cooperate with the proximal portion 142 to prevent the relative rotation of the distal portion 140 relative to the proximal portion 142. Each of the first flat portion 152a and the second flat portion 152b can include a flange 153. The flange 153 can cooperate with a portion of the housing 70 to assist in coupling the coupling portion 152 to the housing 70 (FIG. 13).

The proximal portion 142 can enclose the drive system 90, and can be coupled to the distal portion 140. With reference to FIG. 11, the proximal portion 142 can include a first handle portion 154, a second handle portion 156, a handle retaining portion 158 and a guide 160. With regard to FIG. 12, the first handle portion 154 can define a first or distal end 162, a second or proximal end 164, a passage or throughbore 166 and a cavity 168. The first handle portion 154 can also include one or more indentations 154a, which can facilitate the user grasping the inserter 12. Referring back to FIG. 11, the distal end 162 can include a collar 170, a ledge 172 and a slot 173. The collar 170 can be substantially C-shaped. The collar 170 can include a plurality of threads 170a and an opening 170b. The plurality of threads 170a can couple the handle retaining portion 158 to the first handle portion 154. The opening 170b can receive a portion of the second handle portion 156 to couple the second handle portion 156 to the first handle portion 154. The ledge 172 can mate with the second handle portion 156 to assist in coupling the second handle portion 156 to the first handle portion 154. The slot 173 can be defined from the distal end 162 to an area adjacent to the proximal end 164. The slot 173 can receive the second handle portion 156 to couple the second handle portion 156 to the first handle portion 154.

With reference to FIGS. 11 and 12, the proximal end 164 of the first handle portion 154 can include a groove 174. The groove 174 can be sized such that the lip 133 of the activation device 92 can be received over the groove 174 to assist in coupling the activation device 92 to the first handle portion 154.

With continued reference to FIG. 12, the throughbore 166 can extend from the distal end 162 to the proximal end 164. The throughbore 166 can have a first portion 166a defined adjacent to the distal end 162, from the distal end 162 to the cavity 168, and a second portion 166b, adjacent to the proximal end 164, from the proximal end 164 to the cavity 168. The first portion 166a can be sized to receive the coupling portion 152, a portion of the attachment system 66, a portion of the active angle system 68 therethrough, and the guide 160. The second portion 166b can be sized to receive a portion of the attachment system 66 therethrough, along with a portion of the driver 114.

The cavity 168 can be defined between the first portion 166a and the second portion 166b of the throughbore 166. The cavity 168 can be sized to receive a portion of the driver 114 and the proximal end 96 of the active arm 86 and the proximal end 106 of the passive arm 88. The cavity 168 can cooperate with the shoulders 100, 110 of the active arm 86 and passive arm 88 to limit the motion of the active arm 86 and passive arm 88 relative to the housing 70. With reference to FIG. 13, the cavity 168 can also include an annular recess 169, which can receive the annular projection 126 of the pivoting link 116 to the first handle portion 154. The cavity 168 can movably or pivotably receive the annular projection 126 of the pivoting link 116 to enable the pivoting link 116 to move or pivot relative to the first handle portion 154.

With regard to FIGS. 11 and 13, the second handle portion 156 can be coupled to the first handle portion 154 to enclose the cavity 168. The second handle portion 156 can include a projection 176, a lip 178 (FIG. 13) and an alignment device 179. The projection 176 can be received within the opening 170b of the collar 170. The lip 178 can be formed at an end 156a and can be received within a recess 181 defined in the first handle portion 154. The projection 176 and the lip 178 can assist in coupling the second handle portion 156 to the first handle portion 154. The alignment device 179 can include an arm 183. The arm 183 can have a projection 183a, which can engage the groove 79 of the rod 72 to assist in aligning the rod 72. The arm 183 can be coupled to the second handle portion 156 via a mechanical fastener 185.

The handle retaining portion 158 can couple the distal portion 140 of the housing 70 to the proximal portion 142 of the housing 70. The handle retaining portion 158 can be generally annular, and can taper from a first end 158a to a second end 158b. The handle retaining portion 158 can include a bore 180. The bore 180 can include a first portion 180a and a second portion 180b. The first portion 180a can have a diameter sized to fit around the coupling portion 152 and a portion of the attachment system 66. The second portion 180b can be sized to fit over the flange 153 of the distal portion 140 and can include a plurality of threads. The plurality of threads can threadably engage the plurality of threads 170a of the collar 170 to couple handle retaining portion 158 to the proximal portion 142 of the housing 70. As the flange 153 of the distal portion 140 can be received within the bore 180, the handle retaining portion 158 can couple the distal portion 140 of the housing 70 to the proximal portion 142 of the housing 70. Similarly, with regard to FIG. 13, as the projection 176 of the second handle portion 156 can be received within the opening 170b of the collar 170, the handle retaining portion 158 can also couple the second handle portion 156 to the first handle portion 154.

With reference to FIG. 11, the guide 160 can be received within the first portion 166a of the throughbore 166. The guide 160 can assist in directing the movement of the active arm 86, passive arm 88 and rod 72 within the housing 70. The guide 160 can include a first arm slot 184, a second arm slot 186 and a bore 188. The first arm slot 184 can be generally opposite the second arm slot 186. The first arm slot 184 and the second arm slot 186 can be substantially U-shaped to receive a respective one of the active arm 86 and the passive arm 88. The bore 188 can be defined between the first arm slot 184 and the second arm slot 186. The bore 188 can slidably receive the rod 72 therethrough.

In one exemplary method, with continued reference to FIG. 11, in order to assemble the inserter 12, the driver 114 can be positioned within the first handle portion 154, so that the activation device 92 can be coupled to the driver 114. Then, with the guide 160 coupled to the housing 70 along with the pivoting link 116, the active arm 86 can be inserted into the cavity 168 and through the throughbore 166. The active arm 86 can be placed into driving engagement with the driver 114. Then, the passive arm 88 can be positioned within the cavity 168 and directed through the throughbore 166. The rod 72 can be passed through the first handle portion 154 and the driver 114 so that the knob 74 can be coupled to the rod 72.

Next, the distal portion 140 of the housing 70 can be coupled to the proximal portion 142 so that the coupling portion 152 is received within the throughbore 166, and the rod 72 can pass through the cannulated bore 150 of the distal portion 140. The active arm 86 and the passive arm 88 can be positioned within a respective one of the first arm guide 146 and the second arm guide 148. Then, the second handle portion 156 can be coupled to the first handle portion 154. The handle retaining portion 158 can pass over the distal portion 140 until the handle retaining portion 158 is threadably engaged with the collar 170 to couple the distal portion 140 to the proximal portion 142, and the second handle portion 156 to the first handle portion 154.

With the inserter 12 assembled, with reference to FIG. 12, the curved spacer 10 can be coupled to the inserter 12. In order to couple the curved spacer 10 to the inserter 12, the plurality of threads 80a of the rod 72 can be threadably engaged with the plurality of threads 46a of the coupling portion 16 by rotating the knob 74. In order to move or pivot the curved spacer 10 relative to the inserter 12, the activation device 92 can be rotated in a first direction. The rotation of the activation device 92 can cause the rotation of the driver 114. The rotation of the driver 114 can cause the linear translation of the active arm 86 in the first direction. The pivoting link 116 can transfer the linear translation of the active arm 86 to the passive arm 88, which can cause the passive arm 88 to move in an opposite, second direction (FIG. 14). The linear translation of the active arm 86 can cause the distal end 94 of the active arm 86 to apply a force against the pocket 42 of the curved spacer 10 to pivot the curved spacer 10. The reciprocal movement of the passive arm 88 can move the distal end 104 of the passive arm 88 rearward, towards the inserter 12, to enable the curved spacer 10 to rotate. In one example, with reference to FIG. 15, the curved spacer 10 can be positioned at an angle B, which can be about 25 degrees relative to the inserter 12.

In another example, the activation device 92 can be rotated in a second direction. The rotation of the activation device 92 in the second direction can cause the active arm 86 to move in the second direction, and the passive arm 88 to move in an opposite, first direction. In one example, with reference to FIG. 16, the curved spacer 10 can be positioned at an angle C, which can be about 80 degrees relative to the inserter 12.

Figure 15:
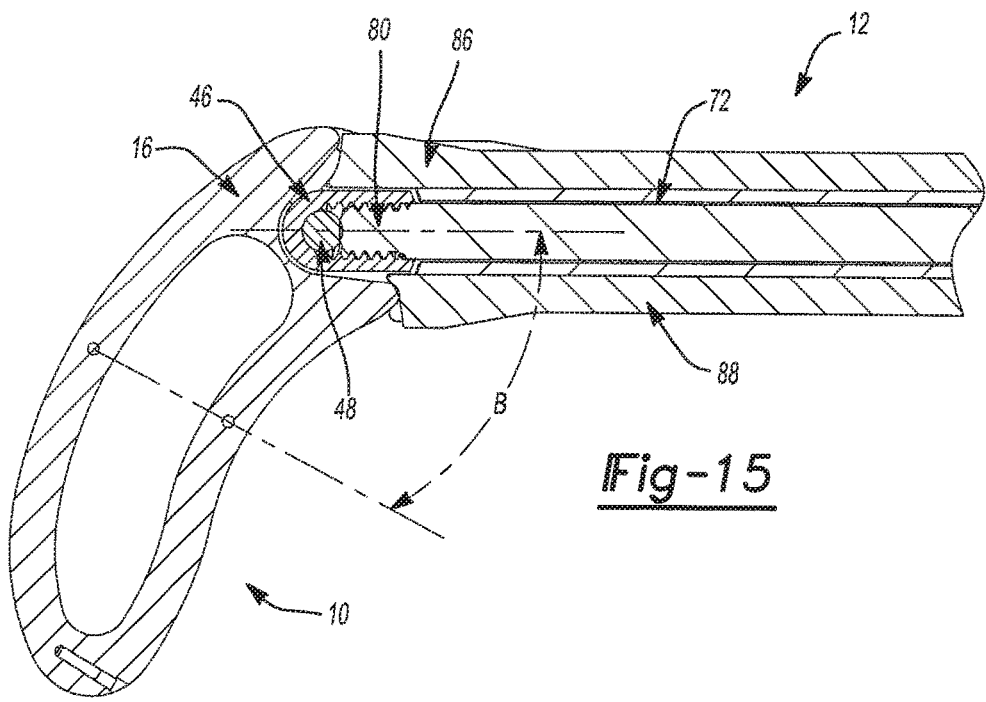
FIG. 15 is a partial cross-sectional view of the curved spacer and inserter of FIG. 1, illustrating the curved spacer positioned at a first angle relative to the inserter.
Figure 16:
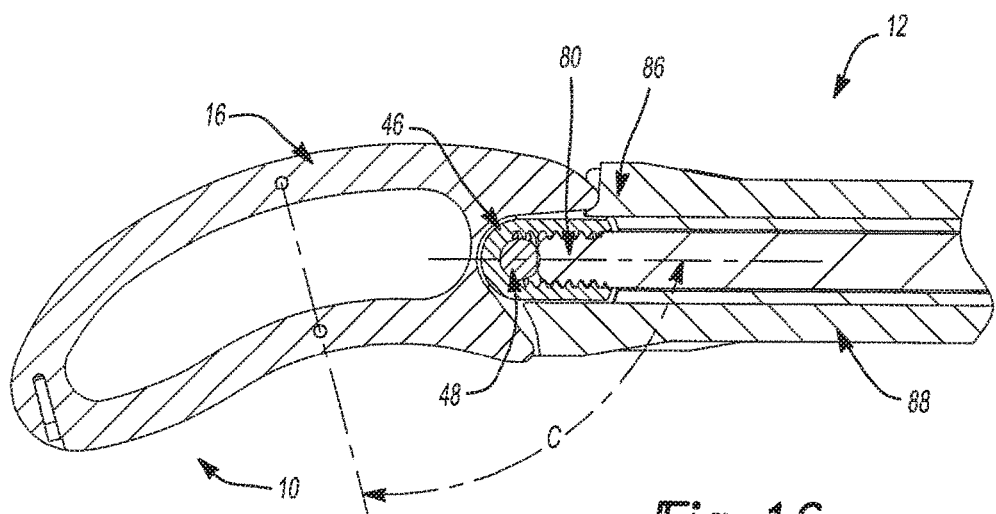
FIG. 16 is a partial cross-sectional view of the curved spacer and inserter of FIG. 1, illustrating the curved spacer positioned at a second angle relative to the inserter.

Thus, the inserter 12 can be used to navigate the curved spacer 10 through the anatomy. In one example, with a small incision formed near the intervertebral disc space and a window formed in a disc annulus, the curved spacer 10 can be positioned at about 80 degrees relative to the inserter 12 (FIG. 16). The inserter 12 can guide the curved spacer 10 through the window in the disc annulus, and then, the activation device 92 can be rotated to place the curved spacer 10 at about 25 degrees relative to the inserter 12 (FIG. 15). By allowing the curved spacer 10 to be positioned at about 25 degrees relative to the inserter 12, the curved spacer 10 can be placed along the curved anterior portion of the vertebral body V to restore disc height, while stabilizing the vertebral body V for long-term spinal fusion (FIG. 2).

With reference now to FIGS. 17-21, in one example, an inserter 200 can be employed with the curved spacer 10 to navigate the curved spacer 10 through the anatomy. As the inserter 200 can be similar to the inserter 12 described with reference to FIGS. 1-16, only the differences between the inserter 12 and the inserter 200 will be discussed in great detail herein, and the same reference numerals will be used to denote the same or similar components. The inserter 200 can be composed of any biocompatible material, such as a biocompatible metal or polymer. In one example, the inserter 200 can comprise a variable angle inserter, which can enable a user to position the curved spacer 10 at a selected angle for the insertion of the curved spacer 10 into the anatomy, as will be discussed. The inserter 200 can comprise an attachment system 202 and a housing 206.

Figure 18:
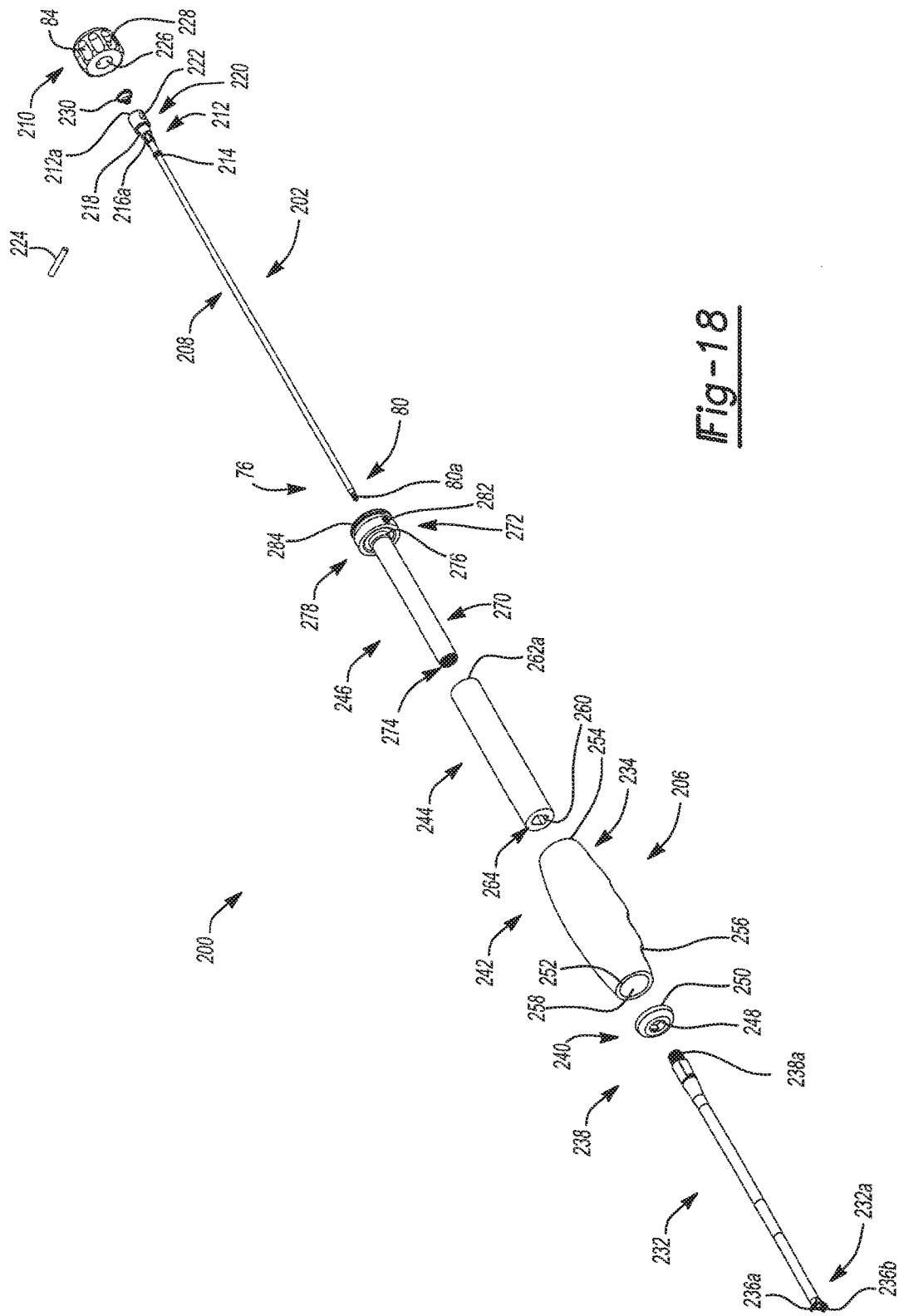
FIG. 18 is an exploded view of the inserter of FIG. 17.

With reference to FIG. 18, the attachment system 202 can couple the curved spacer 10 to the inserter 200. The attachment system 202 can include a rod 208 and a knob 210. The rod 208 can include the first or distal end 76 and a second or proximal end 212. The proximal end 212 can include a plurality of threads 214, a first collar 216, a second collar 218 and a third collar 220. The plurality of threads 214 can serve as a stop for the movement of the rod 208 within the housing 206. The first collar 216 can have a plurality of projections 216a. The second collar 218 can be cylindrical and substantially smooth. The second collar 218 can be formed between the first collar 216 and the third collar 220. The third collar 220 can be located at a proximalmost end 212a of the rod 208. The third collar 220 can include an elongated slot 222, which can be defined in a direction substantially perpendicular to a longitudinal axis of the rod 208. The elongated slot 222 can receive a pin 224, which can couple the knob 210 to the rod 208 (FIG. 20). The elongated slot 222 can enable the pin 224 to move along the elongated slot 222 to absorb forces during impaction of the knob 210.

With regard to FIG. 18, the knob 210 can enable the user to rotate the rod 208 to couple or uncouple the curved spacer 10 from the inserter 200. The knob 210 can include a counterbore 226, a pin bore 228, a biasing member or spring 230 and the graspable portion 84. With reference to FIG. 20, the counterbore 226 can receive the proximalmost end 212a of the rod 208. With reference now to FIG. 21, the pin bore 228 can receive the pin 224 therethrough to couple the rod 208 to the knob 210. The spring 230 can be retained within the counterbore 226, rearward or proximal of the pin bore 228 (e.g., away from the distal end of the rod 208). The spring 230 can prevent the knob 210 from rattling around when the instrument is manipulated. The knob 210 can translate relative to the rod 208 against a bias of the spring 230. In this manner, impact forces delivered to the knob 210 are shielding from the rod 208 and thus the implant. Impact forces are redirected to the support shaft 246.

Generally, the knob 210 can be rotated in one direction to thread the threaded portion 80 into engagement with the coupling portion 16 of the curved spacer 10 to couple the curved spacer 10 to the inserter 200. In order to disengage the curved spacer 10 from the inserter 200, the knob 210 can be rotated in an opposite direction to remove the threaded portion 80 from the coupling portion 16 to disengage the curved spacer 10 from the inserter 200.

Figure 17:
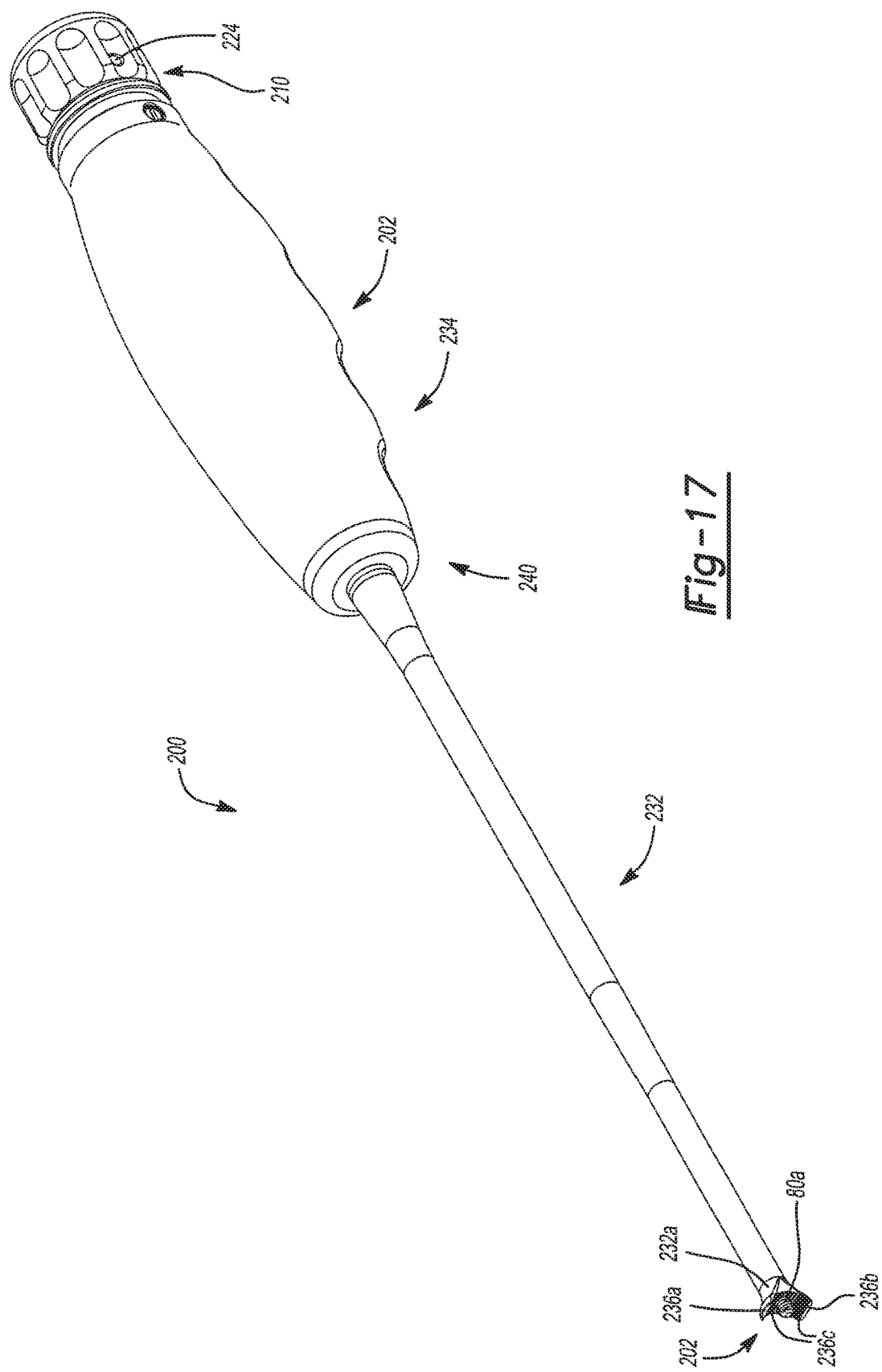
FIG. 17 is perspective view of another exemplary inserter for use with the curved spacer according to the present teachings.

With regard to FIG. 18, the housing 206 can enclose at least a portion of the attachment system 202. The housing 206 can also provide a graspable portion for the user. The housing 206 can include a first or distal portion 232 and a second or proximal portion 234. The distal portion 232 of the housing 206 can be elongated. As best illustrated in FIG. 17, the distalmost end 232a of the distal portion 232 can include a first curved surface 236a opposite a second curved surface 236b. The first curved surface 236a and the second curved surface 236b can correspond to a shape of the proximal end 20 of the curved spacer 10 and can include a plurality of teeth 236c. The plurality of teeth 236c can frictionally engage the proximal end 20 of the curved spacer 10 to assist in fixedly coupling the curved spacer 10 to the inserter 200. With reference to FIG. 18, the distal portion 232 can also include a coupling portion 238. The coupling portion 238 can comprise a plurality of threads 238a. The plurality of threads 238a can be used to couple the distal portion 232 to the proximal portion 234.

The proximal portion 234 can enclose a portion of the attachment system 202. The proximal portion 234 can include a retaining portion 240, a graspable portion 242, a first support shaft 244 and a second support shaft 246. The retaining portion 240 can assist in coupling the distal portion 232 to the proximal portion 234. The retaining portion 240 can be annular. The retaining portion 240 can include a bore 248 and a lip 250. With reference to FIG. 20, the bore 248 can be defined through the retaining portion 240 and can enable a portion of the distal portion 232 to pass through the retaining portion 240. The lip 250 can be sized so that the retaining portion 240 can be press or snap-fit onto a first end 252 of the graspable portion 242.

The graspable portion 242 can include the first end 252, a second end 254, one or more indentations 256 and a throughbore 258. The second end 254 can be opposite the first end 252. The indentations 256 can provide a graspable surface for the user. The throughbore 258 can be defined through the graspable portion 242 from the first end 252 to the second end 254. The throughbore 258 can receive the first support shaft 244 and the second support shaft 246.

The first support shaft 244 can be wholly received within the throughbore 258. The first support shaft 244 can include a first end 260, a second end 262 and a throughbore 264. The first end 260 can be positioned adjacent the first end 252 of the graspable portion 242 when the first support shaft 244 is coupled to the graspable portion 242. The second end 262 can be positioned adjacent to a portion of the second support shaft 246. With regard to FIG. 20, the throughbore 264 can have a first portion 264a at the first end 260, and a second portion 264b, which can extend from an area adjacent to the first end 260 to an area adjacent to the second end 262. The throughbore 264 can also include a third portion 264c at the second end 262. The first portion 264a can be rectangular in shape to receive a portion of the distal portion 232 of the housing 206 (FIG. 18). The second portion 264b can be circular in shape, and can receive a portion of the second support shaft 246. The third portion 264c can be circular in shape and can have a diameter greater than a diameter of the second portion 264b. The third portion 264c can assist in coupling the second support shaft 246 to the graspable portion 242.

The second support shaft 246 can be partially received within the first support shaft 244. Referring to FIG. 18, the second support shaft 246 can include a distal portion 270, a proximal portion 272 and a bore 274. The distal portion 270 can be received within the first support shaft 244. The distal portion 270 can be substantially cylindrical in shape, and can have a diameter, which can be smaller than a diameter of the proximal portion 272.

The proximal portion 272 can include a first collar 276 and a second collar 278. The first collar 276 can be received within the third portion 264c of the throughbore 264. With regard to FIG. 21, the second collar 278 can include a first coupling bore 280, a second coupling bore 282 and a groove 284. The first coupling bore 280 and the second coupling bore 282 can be defined in a direction substantially perpendicular to the bore 274. Each of the first coupling bore 280 and the second coupling bore 282 can extend to the bore 274 and can include a plurality of threads 280a, 282a. The plurality of threads 280a, 282a can each threadably receive a mechanical fastener 285. The groove 284 can provide a graspable surface.

Referring to FIGS. 20 and 21, the bore 274 can be sized to receive a portion of the housing 206 and the attachment system 202 therethrough. The bore 274 can include a plurality of threads 286 at a distalmost end 270a of the distal portion 270. The plurality of threads 286 can threadably engage the coupling portion 238 of the distal portion 232 of the housing 206. The bore 274 can include a plurality of threads 288 at the proximal portion 272. The plurality of threads 288 can cooperate with the plurality of threads 214 of the rod 208 to limit the motion of the rod 208 within the housing 206.

In one exemplary method, with regard to FIG. 18, in order to assemble the inserter 200, the rod 208 can be inserted through the second support shaft 246. The second support shaft 246 can be inserted into the first support shaft 244, and then the first support shaft 244 can be inserted into the graspable portion 242. The mechanical fasteners 285 can then be inserted into the coupling bores 280, 282 (FIG. 21).

With the retaining portion 240 disposed over the distal portion 232 of the housing 206, the distal portion 232 can be positioned into the graspable portion 242 and threadably engaged with the second support shaft 246. The retaining portion 240 can then be snapped into the first end 252 of the graspable portion 242. With the spring 230 positioned within the counterbore 226 of the knob 210, the knob 210 can be positioned about the third collar 220 of the rod 208. The pin 224 can be inserted into the pin bore 228 and through the elongated slot 222 to couple the knob 210 to the rod 208.

With the inserter 200 assembled, the curved spacer 10 can be coupled to the inserter 200 at a desired angle. In one example, similar to the inserter 12, the curved spacer 10 can be coupled to the inserter 200 at about a 25 degree angle. In order to couple the curved spacer 10 to the inserter 12, the plurality of threads 80a of the rod 208 can be threadably engaged with the plurality of threads 46a of the coupling portion 16 by rotating the knob 210. With the curved spacer 10 coupled to the inserter 200, the inserter 200 can be used to navigate the curved spacer 10 through the anatomy, as discussed with regard to the inserter 12, above. In another example, the curved spacer 10 can be coupled to the inserter 200 at about an 80 degree angle. In order to couple the curved spacer 10 to the inserter 12, the plurality of threads 80a of the rod 208 can be threadably engaged with the plurality of threads 46a of the coupling portion 16 by rotating the knob 210.

With reference now to FIGS. 22-26, in one example, an inserter 300 can be employed with the curved spacer 10 to navigate the curved spacer 10 through the anatomy. As the inserter 300 can be similar to the inserter 200 described with reference to FIGS. 17-21, only the differences between the inserter 200 and the inserter 300 will be discussed in great detail herein, and the same reference numerals will be used to denote the same or similar components. The inserter 300 can be composed of any biocompatible material, such as a biocompatible metal or polymer. In one example, the inserter 300 can comprise a fixed angle inserter, which can enable a user to position the curved spacer 10 at a fixed angle for the insertion of the curved spacer 10 into the anatomy, as will be discussed. The inserter 300 can comprise an attachment system 302 and a housing 306.

Figure 23:
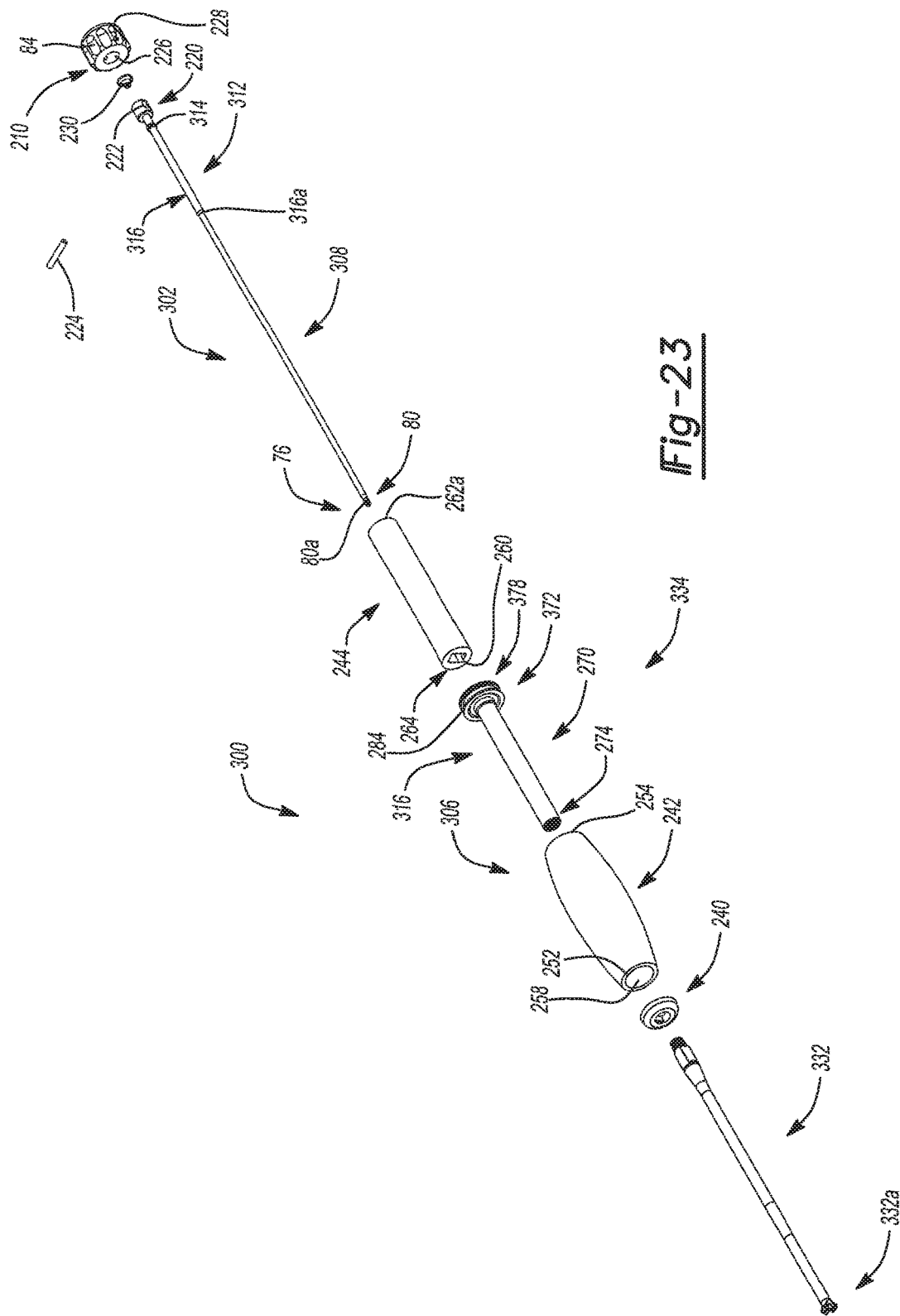
FIG. 23 is an exploded view of the inserter of FIG. 22.

The attachment system 302 can couple the curved spacer 10 to the inserter 300. With reference to FIG. 23, the attachment system 302 can include a rod 308 and the knob 210. The rod 308 can include the first or distal end 76 and a second or proximal end 312. The proximal end 312 can include a plurality of threads 314, a first raised portion 316 and the third collar 220. The plurality of threads 314 can serve as a stop for the movement of the rod 308 within the housing 306. The plurality of threads 314 can be formed on the first raised portion 316. The first raised portion 316 can also define a tapered portion 316a. The tapered portion 316a can contact a portion of the housing 306 to limit the motion of the rod 308 within the housing 306.

The housing 306 can enclose at least a portion of the attachment system 302. The housing 306 can also provide a graspable portion for the user. The housing 306 can include a first or distal portion 332 and a second or proximal portion 334. The distal portion 332 of the housing 306 can be elongated. As best illustrated in FIG. 22, the distal mast end 332a of the distal portion 332 can include a first curved surface 336a opposite a second curved surface 336b. The distal portion 332 can also include coupling portion 238. The first curved surface 336a can be opposite the second curved surface 336b. The first curved surface 336a and the second curved surface 336b can correspond to a shape of the proximal end 20 of the curved spacer 10. Each of the first curved surface 336a and the second curved surface 336b can include an anti-rotation nub 338a, 338b.

The anti-rotation nub 338a, 338b can protrude from the first curved surface 336a and the second curved surface 336b and can engage the main body 14 of the curved spacer 10. The engagement between the anti-rotation nub 338a, 338b and the main body 14 can prevent the main body 14 from moving or rotating relative to the inserter 300. In one example, the anti-rotation nub 338a can extend a greater distance than the anti-rotation nub 338b to enable the inserter 300 to be attached at one of two preferred angles. In this regard, in one example with reference to FIG. 27, if the curved spacer 10 is coupled to the inserter 300 in a first orientation, the curved spacer 10 can be orientated at an angle FA of about 70 degrees relative to the inserter 300. If the inserter 300 is rotated about 180 degrees relative to the curved spacer 10, then with reference to FIG. 28, the curved spacer 10 can be orientated at an angle FB of about 45 degrees relative to the inserter 300. It should be noted that these preferred angles are merely exemplary, as the anti-rotation nub 338a, 338b could be configured so that the curved spacer 10 could be coupled at any desired angle relative to the inserter 300. As a further example, the anti-rotation nubs 338a, 338b can be formed so that the curved spacer 10 remains in the same orientation regardless of how the curved spacer 10 is coupled to the inserter 300.

Referring to FIG. 23, the proximal portion 334 can enclose a portion of the attachment system 302. The proximal portion 334 can include the retaining portion 240, the graspable portion 242, the first support shaft 244 and a second support shaft 346. The second support shaft 346 can be partially received within the first support shaft 244. The second support shaft 346 can include the distal portion 270, a proximal portion 372 and the bore 274. The tapered portion 316a of the first raised portion 316 of the rod 308 can contact the distal portion 270 to prevent the further advancement of the rod 308. The proximal portion 372 can include the first collar 276 and a second collar 378. The second collar 378 can include the groove 284.

In one exemplary method, in order to assemble the inserter 300, the rod 308 can be inserted through the second support shalt 346. The second support shaft 346 can be inserted into the first support shaft 244, and then the first support shaft 244 can be inserted into the graspable portion 242. With the retaining portion 240 disposed over the distal portion 232 of the housing 206, the distal portion 232 can be positioned into the graspable portion 242 and threadably engaged with the second support shaft 346. The retaining portion 240 can then be snapped into the first end 252 of the graspable portion 242. With the spring 230 positioned within the counterbore 226 of the knob 210, the knob 210 can be positioned about the third collar 220 of the rod 308. The pin 224 can be inserted into the pin bore 228 and through the elongated slot 222 to couple the knob 210 to the rod 308.

Figure 27:
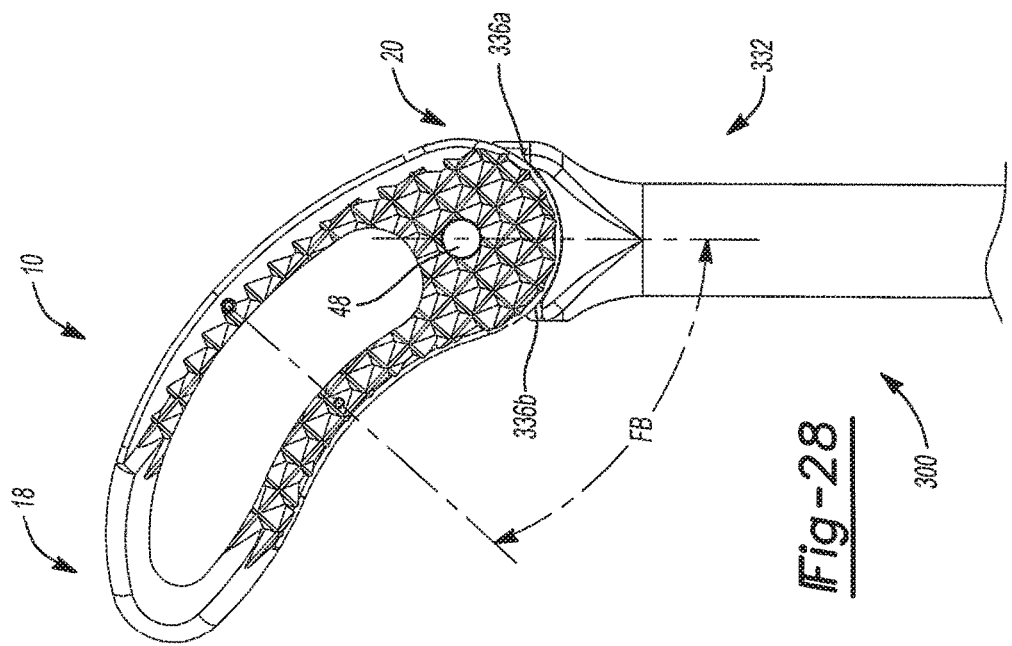
FIG. 27 is a detail view of a portion of the inserter of FIG. 22 coupled to the curved spacer such that the curved spacer is at a first exemplary angle relative to the inserter.
Figure 28:
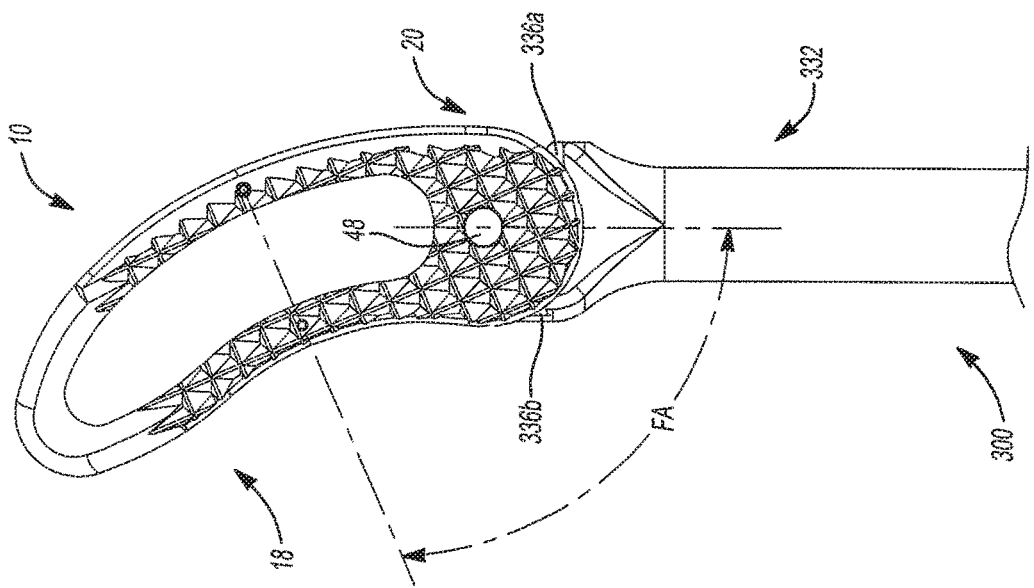
FIG. 28 is a detail view of a portion of the inserter of FIG. 22 coupled to the curved spacer such that the curved spacer is at a second exemplary angle relative to the inserter.
Figure 29:
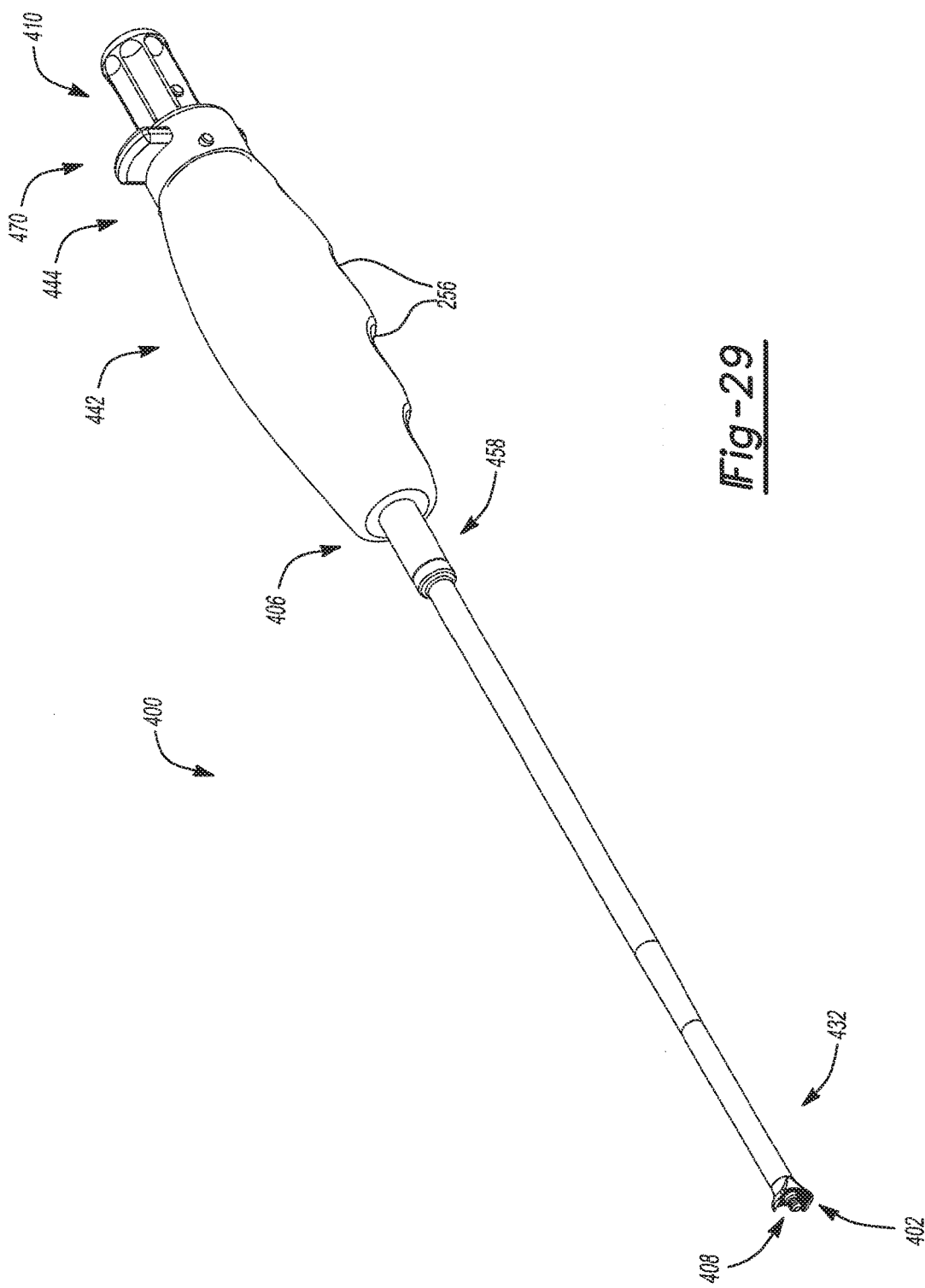
FIG. 29 is perspective view of another exemplary inserter for use with the curved spacer according to the present teachings.
Figure 34:
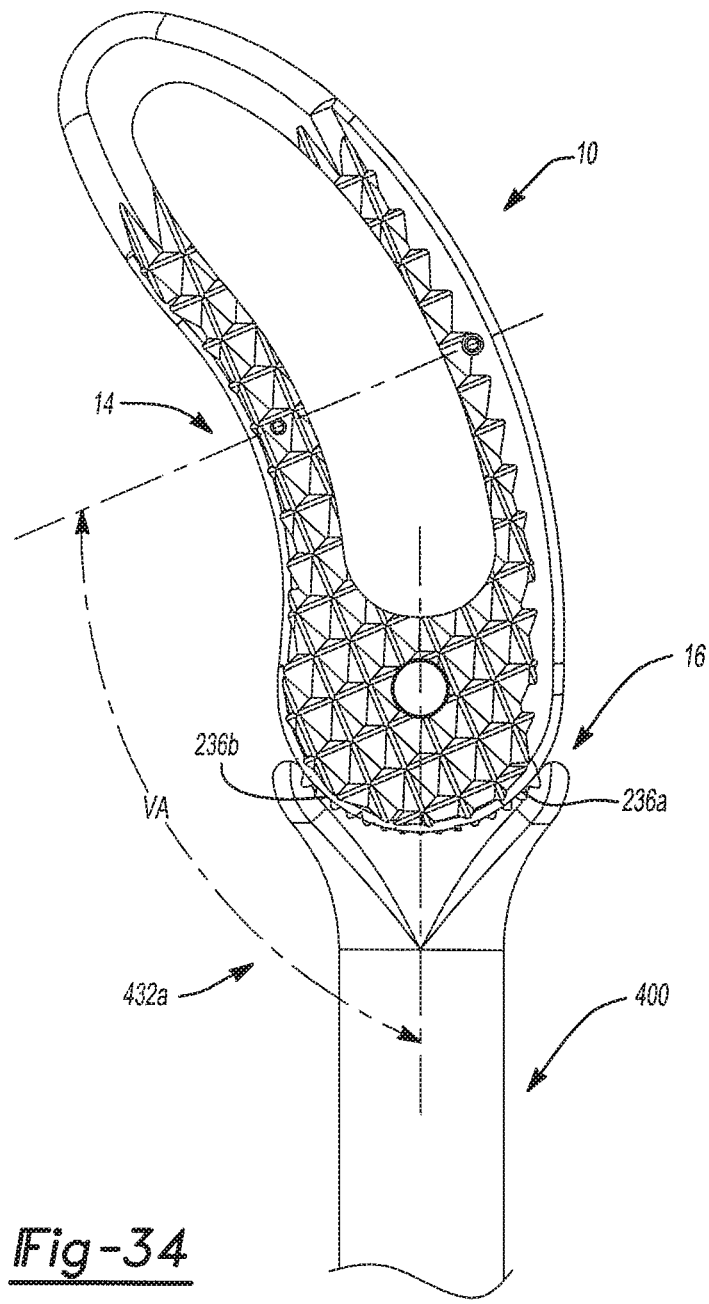
FIG. 34 is a detail view of a portion of the inserter of FIG. 29 coupled to the curved spacer such that the curved spacer is at a first exemplary angle relative to the inserter.
Figure 35:
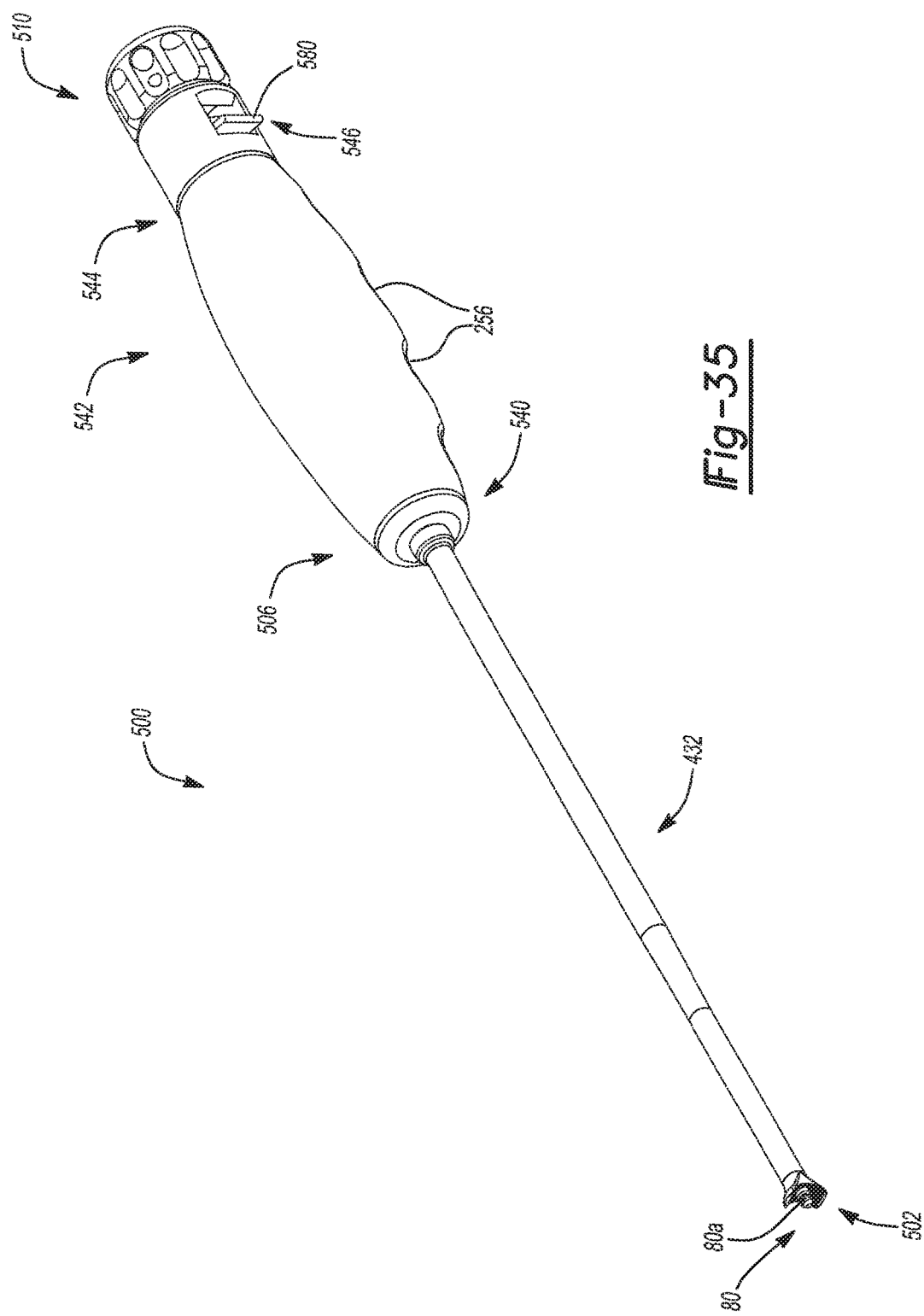
FIG. 35 is perspective view of another exemplary inserter for use with the curved spacer according to the present teachings.

With the inserter 300 assembled, the curved spacer 10 can be coupled to the inserter 300 at the angle defined by the anti-rotation nubs 338a, 338b. In one example, the curved spacer 10 can be coupled to the inserter 300 at about a 70 degree angle (FIG. 27). In order to couple the curved spacer 10 to the inserter 12, the plurality of threads 80a of the rod 308 can be threadably engaged with the plurality of threads 46a of the coupling portion 16 by rotating the knob 210. With the curved spacer 10 coupled to the inserter 300, the inserter 300 can be used to navigate the curved spacer 10 through the anatomy, as discussed with regard to the inserter 12, above.

With reference now to FIGS. 29-34, in one example, an inserter 400 can be employed with the curved spacer 10 to navigate the curved spacer 10 through the anatomy. As the inserter 400 can be similar to the inserter 200 described with reference to FIGS. 17-21, only the differences between the inserter 200 and the inserter 400 will be discussed in great detail herein, and the same reference numerals will be used to denote the same or similar components. The inserter 400 can be composed of any biocompatible material, such as a biocompatible metal or polymer. In one example, the inserter 400 can comprise a variable angle inserter, which can enable a user to lock the curved spacer 10 at a selected angle for the insertion of the curved spacer 10 into the anatomy, as will be discussed. The inserter 400 can comprise an attachment system 402 and a housing 406.

The attachment system 402 can couple the curved spacer 10 to the inserter 400. With reference to FIG. 30, the attachment system 402 can include a rod 408 and a knob 410. The rod 408 can include the first or distal end 76 and a second or proximal end 412. The proximal end 412 can include the plurality of threads 214 and a third collar 420. The third collar 420 can be located at a proximalmost end 412a of the rod 408. The third collar 420 can be elongated, and can include an elongated slot 422, which can be defined in a direction substantially perpendicular to a longitudinal axis of the rod 408. The elongated slot 422 can receive the pin 224, which can couple the knob 410 to the rod 408. The elongated slot 422 can enable the pin 224 to move along the elongated slot 422 to absorb forces during impaction of the knob 410.

The knob 410 can enable the user to rotate the rod 408 to couple or uncouple the curved spacer 10 from the inserter 400. With reference to FIGS. 30 and 32, the knob 410 can include a counterbore 426, a pin bore 428 and a graspable portion 430. The counterbore 426 can receive the proximalmost end 412a of the rod 408. The pin bore 428 can receive the pin 224 therethrough to couple the rod 408 to the knob 410. The graspable portion 430 can provide a surface for the user to manipulate the knob 410.

Generally, the knob 410 can be rotated in one direction to thread the threaded portion 80 of the rod 408 into engagement with the coupling portion 16 of the curved spacer 10 to couple the curved spacer 10 to the inserter 400. In order to disengage the curved spacer 10 from the inserter 400, the knob 410 can be rotated in an opposite direction to remove the threaded portion 80 from the coupling portion 16 to disengage the curved spacer 10 from the inserter 400.

The housing 406 can enclose at least a portion of the attachment system 402. With reference to FIG. 30, the housing 406 can also provide a graspable portion for the user. The housing 406 can include a first or distal portion 432 and a second or proximal portion 434. The distal portion 432 of the housing 406 can comprise an elongated body. The distalmost end 432a of the distal portion 432 can include the first curved surface 236a opposite the second curved surface 236b. The distal portion 432 can also include a coupling portion 438 and a flange 440. The coupling portion 438 can have a diameter sized to enable the coupling portion 438 to be press fit onto the proximal portion 434. The coupling portion 438 can be substantially cylindrical. The flange 440 can be annular, and can be formed about a circumference of the coupling portion 438. The flange 440 can engage a portion of the proximal portion 434 to assist in coupling the distal portion 432 to the proximal portion 434.

The proximal portion 434 can enclose a portion of the attachment system 402. The proximal portion 434 can include a graspable portion 442 and a locking portion 444. The graspable portion 442 can include a first end 452, a second end 454, the one or more indentations 256 and a throughbore 456. The first end 452 can include a substantially cylindrical projection 458. The cylindrical projection 458 can be sized to enable the coupling portion 438 to be press-fit therein. The flange 440 of the distal portion 432 can be engaged with a distalmost end 458a of the cylindrical projection 458 to assist in coupling the distal portion 432 to the proximal portion 434. The second end 454 can be opposite the first end 452.

With reference to FIG. 32, the second end 454 can be coupled to the locking portion 444. The second end 454 can include a cylindrical protrusion 460. The cylindrical protrusion 460 can extend outwardly from the second end 454. The cylindrical protrusion 460 can have a diameter less than a diameter of the graspable portion 442. The cylindrical protrusion 460 can include a bore 460a. The bore 460a can receive a pin 462, which can couple the locking portion 444 to the graspable portion 442. The throughbore 456 can be defined through the graspable portion 442 from the first end 452 to the second end 454. The throughbore 456 can be sized to enable the rod 408 to pass through the graspable portion 442.

With regard to FIG. 30, the locking portion 444 can be substantially cylindrical. The locking portion 444 can include a first end 464, a second end 466, a central bore 468 and a locking tab 470. Referring to FIG. 32, the first end 464 can be coupled to the cylindrical protrusion 460 and positioned adjacent to the second end 454 of the graspable portion 442. The first end 464 can include an aperture 472. The aperture 472 can be defined in a direction substantially perpendicular to the central bore 468. The aperture 472 can receive the pin 462 therethrough to couple the locking portion 444 to the graspable portion 442.

The second end 466 can be adjacent to the knob 410 when the attachment system 402 is coupled to the housing 406. The second end 466 can include a locking slot 474. The locking slot 474 can be defined through the locking portion 444. The locking slot 474 can be defined so as to be substantially perpendicular to the central bore 468. The locking slot 474 can receive the locking tab 470.

The central bore 468 can pass through the first end 464 to the second end 466. The central bore 468 can enable the rod 408 to pass through the locking portion 444. At the first end 464, the central bore 468 can also be sized to receive the cylindrical protrusion 460. At the second end 466, the central bore 468 can be sized to receive the third collar 420.

With regard to FIG. 33, the locking tab 470 can be received within the locking slot 474. The locking tab 470 can include a first surface 478, a second surface 480 and a bore 482. The first surface 478 can include a spring 484. The spring 484 can bias against a portion of the locking slot 474 to apply tension to the rod 408. The second surface 480 can be opposite the first surface 478. The second surface 480 can define a ramp 480a. The ramp 480a can be formed about a portion of the bore 482. The ramp 480a can cooperate with the spring 484 to apply tension to the rod 408. The application of tension to the rod 408 can further couple the curved spacer 10 to the inserter 400. The bore 482 can be elongated to enable the locking tab 470 to move relative to the rod 408 within the locking slot 474.

In one exemplary method, with reference to FIG. 30, in order to assemble the inserter 400, the distal portion 432 can be coupled to the graspable portion 442 of the housing 406. Then, the locking portion 444 can be coupled to the graspable portion 442 of the housing 406 by inserting the pin 462 through the aperture 472. The locking tab 470 can be positioned within the locking slot 474 so that the bore 482 is substantially coaxially aligned with the throughbore 456 of the graspable portion 442. Next, the rod 408 can be inserted through the housing 406. The knob 410 can be positioned over the third collar 220 of the rod 408 and the pin 224 can be inserted through the pin bore 428 and the elongated slot 222 to couple the knob 410 to the rod 408.

With the inserter 400 assembled, the curved spacer 10 can be coupled to the inserter 400 at a desired angle. In one example, with reference to FIG. 34, the curved spacer 10 can be coupled to the inserter 400 at an angle VA of about a 80 degree angle. In order to couple the curved spacer 10 to the inserter 400, the plurality of threads 80a of the rod 408 can be threadably engaged with the plurality of threads 46a of the coupling portion 16 by rotating the knob 410. Then, the locking tab 470 can be advanced through the locking slot 474 to apply tension to the rod 408. The application of tension to the rod 408 can fixedly couple or lock the curved spacer 10 to the inserter 400. With the curved spacer 10 fixedly coupled to the inserter 400, the inserter 400 can be used to navigate the curved spacer 10 through the anatomy, as discussed with regard to the inserter 12, above.

In use, if it is desired to change the angle of the curved spacer 10 relative to the inserter 400, the locking tab 470 can be moved in the locking slot 474 to release the tension on the rod 408. Then, the curved spacer 10 can be moved to another selected angle, such as about a 25 degree angle, for example. Then, the locking tab 470 can be advanced through the locking slot 474 to apply tension to the rod 408 to fixedly couple or lock the curved spacer 10 to the inserter 400.

With reference now to FIGS. 35-39, in one example, an inserter 500 can be employed with the curved spacer 10 to navigate the curved spacer 10 through the anatomy. As the inserter 500 can be similar to the inserter 400 described with reference to FIGS. 29-34, only the differences between the inserter 400 and the inserter 500 will be discussed in great detail herein, and the same reference numerals will be used to denote the same or similar components. The inserter 500 can be composed of any biocompatible material, such as a biocompatible metal or polymer. In one example, the inserter 500 can comprise a variable angle inserter, which can enable a user to lock the curved spacer 10 at a selected angle for the insertion of the curved spacer 10 into the anatomy, as will be discussed. The inserter 500 can comprise an attachment system 502 and a housing 506.

Figure 36:
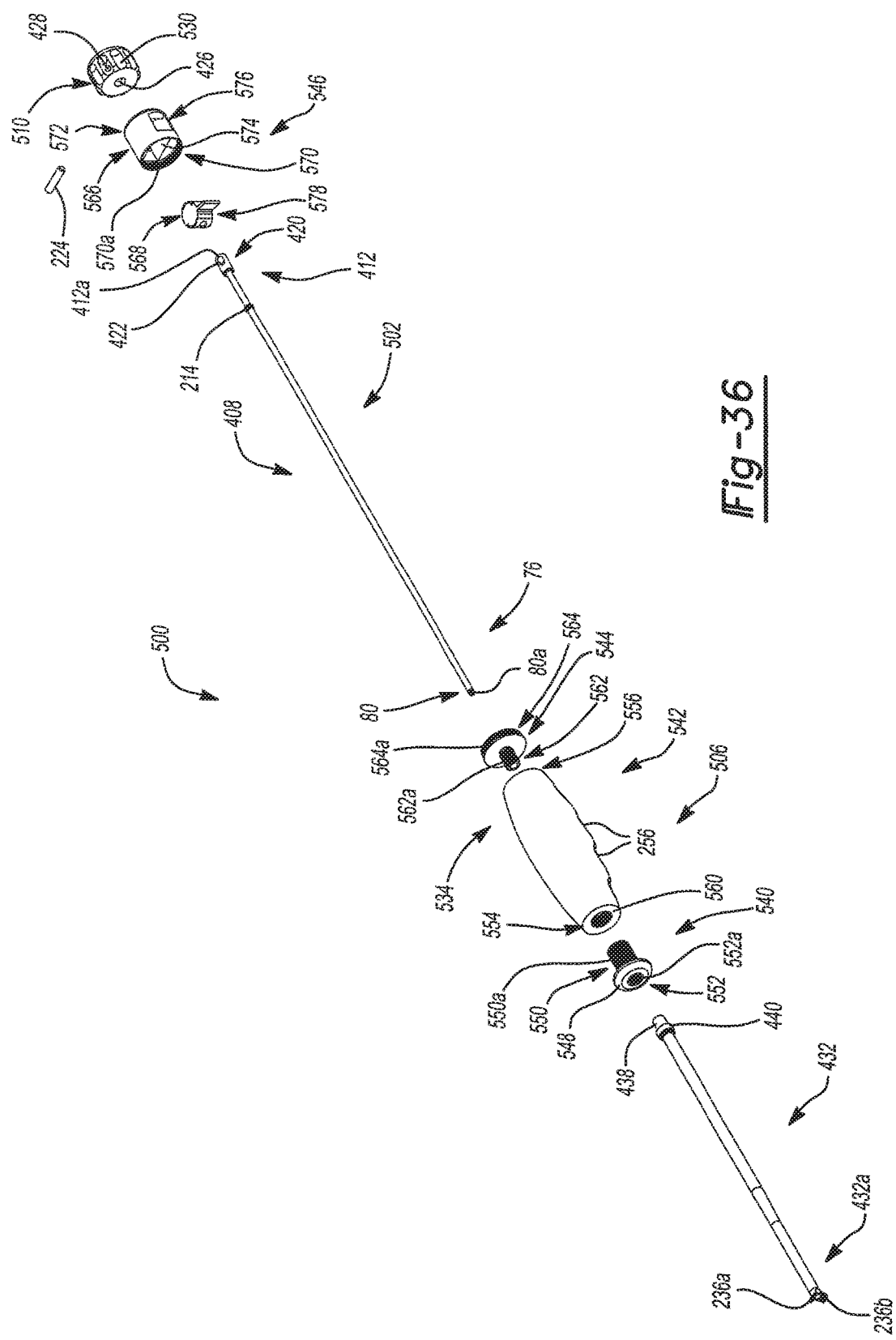
FIG. 36 is an exploded view of the inserter of FIG. 35.
Figure 37:
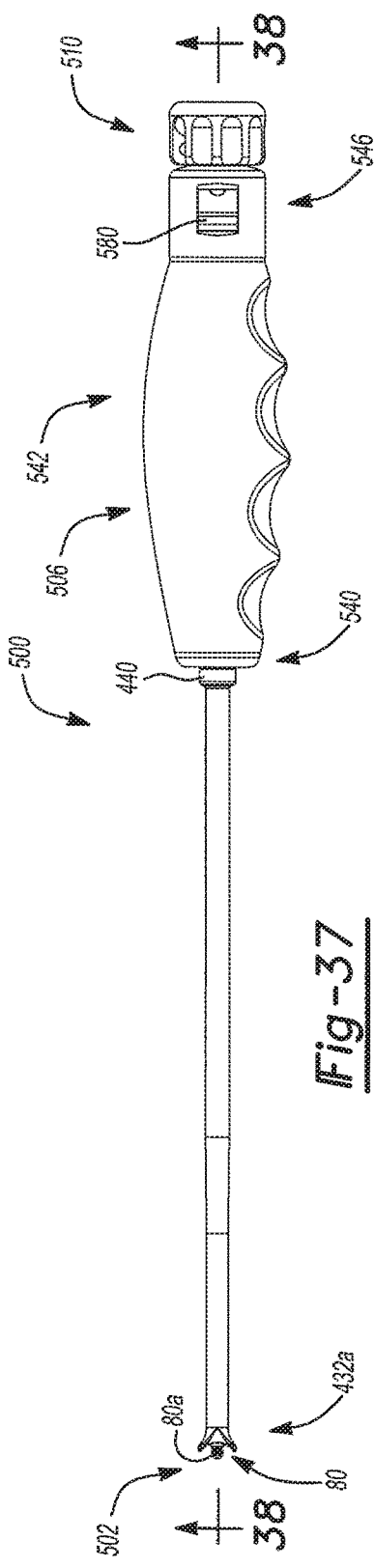
FIG. 37 is a side view of the inserter of FIG. 35.

With reference to FIG. 36, the attachment system 502 can couple the curved spacer 10 to the inserter 500. The attachment system 502 can include the rod 408 and a knob 510. The knob 510 can enable the user to rotate the rod 408 to couple or uncouple the curved spacer 10 from the inserter 500. The knob 510 can include the counterbore 426, the pin bore 428 and a graspable portion 530. The graspable portion 530 can provide a surface for the user to manipulate the knob 510.

The housing 506 can enclose at least a portion of the attachment system 502. The housing 506 can also provide a graspable portion for the user. The housing 506 can include the first or distal portion 432 and a second or proximal portion 534. The proximal portion 534 can enclose a portion of the attachment system 502. The proximal portion 534 can include a coupling portion 540, a graspable portion 542, a base 544 and a locking portion 546. The coupling portion 540 can include an annular portion 548, a projection 550 and a bore 552. The annular portion 548 can have a diameter sized to mate with a first end 554 of the graspable portion 542.

Figure 38:
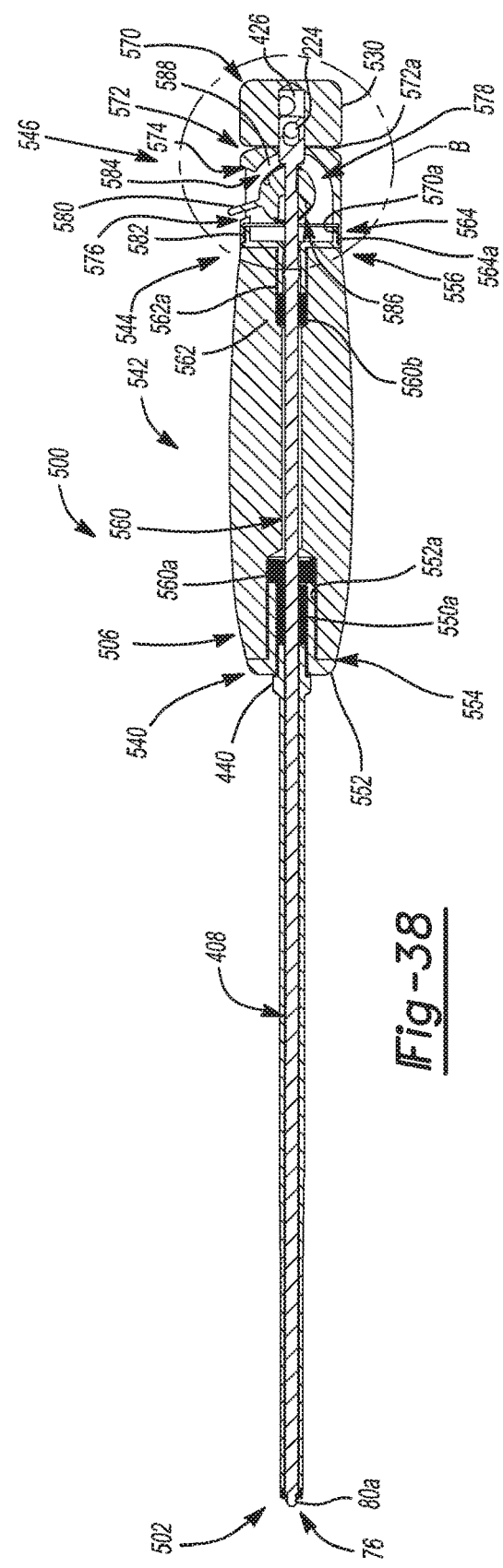
FIG. 38 is a cross-sectional view of the curved spacer and inserter of FIG. 35, taken along line 38-38 of FIG. 37.

The projection 550 can extend outwardly from the annular portion 548 and can have a diameter smaller than a diameter of the annular portion 548 to enable the projection 550 to be received within the graspable portion 542. The projection 550 can have a plurality of threads 550a, which can threadably engage a portion of the graspable portion 542 to couple the coupling portion 540 to the graspable portion 542 (FIG. 38). With reference to FIGS. 36 and 38, the bore 552 can extend through the coupling portion 540 from the annular portion 548 through the projection 550. In one example, the bore 552 can include a plurality of threads 552a, which can enable the coupling portion 438 of the distal portion 432 to be press-fit into the coupling portion 540. It should be noted the bore 552 could also be smooth.

The graspable portion 542 can include a first end 554, a second end 556, the one or more indentations 256 and a throughbore 560. The first end 554 can be adjacent to the coupling portion 540 when the coupling portion 540 is coupled to the graspable portion 542. The second end 556 can be adjacent to the base 544 when the base 544 is coupled to the graspable portion 542. With reference to FIG. 38, the throughbore 560 can extend through the graspable portion 542 from the first end 554 to the second end 556. The throughbore 560 can include a first plurality of threads 560a at the first end 554 and a second plurality of threads 560b at the second end 556. The first plurality of threads 560a can have a diameter sized to threadably engage the plurality of threads 550a of the projection 550 to couple the coupling portion 540 to the graspable portion 542. The second plurality of threads 560b can have a diameter sized to threadably engage a portion of the base 544 to couple the base 544 to the graspable portion 542. The throughbore 560 can also be sized to enable the rod 408 to pass through the graspable portion 542.

Referring to FIGS. 36 and 38, the base 544 can include a projection 562 and an annular portion 564. The projection 562 can extend from the annular portion 564 and can be sized to be received within the throughbore 560 of the graspable portion 542 at the second end 556. The projection 562 can include a plurality of threads 562a, which can threadably engage the second plurality of threads 560b of the throughbore 560 to couple the base 544 to the graspable portion 542. The annular portion 564 can be sized to mate with the second end 556 of the graspable portion 542, and can include a plurality of threads 562a disposed about a periphery or circumference of the annular portion 564. The plurality of threads 562a can couple the locking portion 546 to the base 544.

The locking portion 546 can include a substantially cylindrical housing 566 and a locking tab 568. The housing 566 can have a first or distal end 570, a second or proximal end 572, a cavity 574 and a slot 576. With reference to FIG. 38, the distal end 570 can be configured to be positioned over the annular portion 564 of the base 544 and can include a plurality of threads 570a. The plurality of threads 570a can threadably engage the plurality of threads 562a of the annular portion 564 to threadably couple the housing 566 to the base 544.

With continuing reference to FIG. 38, the second or proximal end 572 can include a bore 572a, which can be sized to enable the third collar 220 of the rod 408 to pass through the housing 566. The cavity 574 can be sized to receive the locking tab 568 so that the locking tab 568 can move or rotate within the cavity 574. The slot 576 can enable a portion of the locking tab 568 to extend beyond the housing 566 to enable a user to manipulate the locking tab 568.

The locking tab 568 can include a cylindrical housing 578 and a tab 580. The cylindrical housing 578 can be received within the cavity 574 such that a longitudinal axis of the cylindrical housing 578 is substantially perpendicular to a longitudinal axis of the inserter 500. As best illustrated in FIG. 39, the cylindrical housing 578 can include a first slot 582, a second slot 584, a first biasing member 586 and a second biasing member 588. The first slot 582 and the second slot 584 can be diametrically opposed from each other within the cylindrical housing 578. The rod 408 can be received through a portion of the first slot 582 and the second slot 584. The first slot 582 and the second slot 584 can be substantially triangular to define a range of movement for the tab 580 about the rod 408, as will be discussed.

The first biasing member 586 and the second biasing member 588 can each be defined along a perimeter 582a, 584a of a respective one of the first slot 582 and second slot 584. The first biasing member 586 and the second biasing member 588 can each include a slot 586a, 588a, which can enable the first biasing member 586 and the second biasing member 588 to move about the rod 408. The first biasing member 586 and the second biasing member 588 can act as a living spring to apply tension to the rod 408. In this regard, when the first biasing member 586 and the second biasing member 588 are moved from a first position to a second position, an end 586b, 588b of each of the first biasing member 586 and the second biasing member 588 can bias against a respective one of the base 544 and the housing 566 to apply tension to the third collar 220 of the rod 408. This can assist in fixedly coupling the curved spacer 10 to the inserter 500.

The tab 580 can be used to move the first biasing member 586 and the second biasing member 588 between the first position and the second position. In one example, in the first position, the tab 580 can be adjacent to a first edge 576a of the slot 576, and in the second position, the tab 580 can be adjacent to a second end 576b of the slot 576. The tab 580 can extend outwardly from the housing 566 and can be integrally formed with the cylindrical housing 578 of the locking tab 568. It should be noted that the tab 580 could be discretely formed and coupled to the locking tab 568 in a post processing step, for example.

In one exemplary method, with reference to FIG. 36, in order to assemble the inserter 500, the coupling portion 540 can be coupled to the first end 554 of the graspable portion 542, and the base 544 can be coupled to the second end 556 of the graspable portion 542. Then, the distal portion 432 can be coupled to the graspable portion 442 of the housing 406. With the locking tab 568 positioned within the housing 566, the housing 566 of the locking portion 546 can be coupled to the base 544. Next, the rod 408 can be inserted through the housing 506. The knob 510 can be positioned over the third collar 220 of the rod 408 and the pin 224 can be inserted through the pin bore 428 and the elongated slot 222 to couple the knob 510 to the rod 408.

With the inserter 500 assembled, the curved spacer 10 can be coupled to the inserter 500 at a desired angle. In one example, the curved spacer 10 can be coupled to the inserter 500 at about a 80 degree angle. As discussed with regard to the inserter 400, in order to couple the curved spacer 10 to the inserter 500, the plurality of threads 80a of the rod 408 can be threadably engaged with the plurality of threads 46a of the coupling portion 16 by rotating the knob 510. Then, the tab 580 of the locking tab 568 can be moved from the first position to the second position to apply tension to the rod 408. The application of tension to the rod 408 can fixedly couple or lock the curved spacer 10 to the inserter 500. With the curved spacer 10 fixedly coupled to the inserter 500, the inserter 500 can be used to navigate the curved spacer 10 through the anatomy, as discussed with regard to the inserter 12, above.

In use, if it is desired to change the angle of the curved spacer 10 relative to the inserter 500, the tab 576 of the locking tab 568 can be moved from the second position to the first position to release the tension on the rod 408. Then, the curved spacer 10 can be moved to another selected angle, such as about a 25 degree angle, for example. Then, the tab 576 of the locking tab 568 can be moved from the first position to the second position to fixedly couple or lock the curved spacer 10 to the inserter 500.

Accordingly, the curved spacer 10 can be coupled to any of the inserters 12, 200, 300, 400, 500 and navigated through the anatomy into the intervertebral disc space. The inserter 12 can enable the user to actively select the angle for the curved spacer 10 relative to the inserter 12, which can allow the user to fully control the angle of the curved spacer 10 throughout the entire implantation process. The inserter 200 can allow the user to couple the curved spacer 10 to the inserter 200 at a desired angle, while the inserter 300 can enable the user to couple the curved spacer 10 to the inserter 300 at a fixed angle. The inserters 400, 500 can allow the user to couple the curved spacer 10 to the inserter 400, 500 at a desired angle, and the curved spacer 10 can then be positioned within the anatomy. Once positioned within the anatomy, the locking tab 470, 568 can be unlocked to enable the inserter 400, 500 to move relative to the curved spacer 10. The locking tab 470, 568 can then be locked, and the curved spacer 10 further positioned within the anatomy. It should be noted that the inserters 12, 200, 300, 400, 500 can be provided individually, or could be each packaged with the curved spacer 10. Alternatively, the inserters 12, 200, 300, 400, 500 could be packaged together with the curved spacer 10 as a kit.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. An instrument for inserting an intervertebral spacer, the instrument comprising:

an elongated body comprising a proximal end, a distal end and a first passage extending from the proximal end to the distal end;

a handle coupled to the proximal end of the elongated body, the handle comprising a proximal end, a distal end, and a second passage extending from the proximal end to the distal end;

a rod receivable through the first passage and the second passage, the rod movable relative to the elongated body and the handle, the rod having a distal end that is removably coupleable to the intervertebral spacer;

a first arm at least partially disposed in the second passage and movable relative to the elongated body, the first arm comprising a distal end with a first curved surface for engaging the intervertebral spacer and a proximal end with an engagement feature and a first link feature;

a second arm at least partially disposed in the second passage and movable relative to the elongated body, the second arm comprising a distal end with a second curved surface for engaging the intervertebral spacer and a proximal end with a second link feature; and a pivoting link disposed within the second passage of the housing, the pivoting link operably coupled to the first link feature and the second link feature such that movement of the first arm in a first direction causes reciprocal movement of the second arm in a second direction opposite the first direction;

wherein, when a driver engages the engagement feature of the first arm to actuate the first arm, and the first curved surface and the second curved surface are engaged with the intervertebral spacer, the reciprocal movement of the first arm and the second arm cooperate to selectively pivot the intervertebral spacer with respect to the instrument.

2. The instrument of claim 1, wherein the driver comprises a cannulated shaft and wherein the rod extends through the cannulated shaft of the driver.

3. The instrument of claim 1, further comprising an activation device operably coupled to the driver such that actuation of the activation device moves the first arm in the first direction and the second arm in the second direction.

4. The instrument of claim 3, wherein the activation device is further coupled to the distal end of the handle.

5. The instrument of claim 1, wherein the first curved surface and the second curved surface each include a plurality of teeth disposed therein for engaging the intervertebral spacer.

6. The instrument of claim 1, wherein the first curved surface and the second curved surface each include an anti-rotation nub that restricts movement of the intervertebral spacer relative to the elongate body.

7. The instrument of claim 1, further comprising a guide positioned within a proximal portion of the first passage of the elongated body.

8. The instrument of claim 7, wherein the guide includes a first arm slot that slidably receives the first arm and a second arm slot that slidably receives the second arm.

9. The instrument of claim 7, wherein the guide includes a bore disposed therein that slidably receives the rod therethrough.

10. An instrument for inserting an intervertebral spacer, the instrument comprising:

an elongated body comprising a first passage extending from a proximal end to a distal end thereof;

a handle coupled to the proximal end of the elongated body, the handle comprising a a second passage extending from a proximal end to a distal end thereof;

a rod receivable through the first passage and the second passage, the rod movable relative to the elongated body and the handle, the rod having a distal end that is removably threadably coupleable to the intervertebral spacer;

a drive arm at least partially disposed in the second passage and movable relative to the elongated body, the drive arm comprising a distal end with a first curved surface for engaging the intervertebral spacer and a proximal end with an engagement feature and a first link feature;

a passive arm at least partially disposed in the second passage and movable relative to the elongated body, the passive arm comprising a distal end with a second curved surface for engaging the intervertebral spacer and a proximal end with a second link feature; and a pivoting link disposed within the second passage of the housing, the pivoting link operably coupled to the first link feature and the second link feature such that movement of the drive arm in a first direction causes reciprocal movement of the passive arm in a second direction opposite the first direction;

wherein, when a driver engages the engagement feature of the drive arm to a actuate the drive arm, and the first curved surface and the second curved surface are engaged with the intervertebral spacer, the reciprocal movement of the drive arm and the passive arm cooperate to selectively pivot the intervertebral spacer with respect to the instrument.

11. The instrument of claim 10, wherein the driver comprises a cannulated shaft and wherein the rod extends through the cannulated shaft of the driver.

12. The instrument of claim 10, further comprising an activation device operably coupled to the driver such that actuation of the activation device moves the drive arm in the first direction and the passive arm in the second direction.

13. The instrument of claim 12, wherein the activation device is further coupled to the distal end of the handle.

14. The instrument of claim 10, wherein the first curved surface and the second curved surface each include a plurality of teeth disposed therein for engaging the intervertebral spacer.

15. The instrument of claim 10, wherein the first curved surface and the second curved surface each include an anti-rotation nub that restricts movement of the intervertebral spacer relative to the elongate body.

16. The instrument of claim 10, further comprising a guide positioned within a proximal portion of the first passage of the elongated body.

17. The instrument of claim 16, wherein the guide includes a drive arm slot that slidably receives the drive arm and a passive arm slot that slidably receives the passive arm.

18. The instrument of claim 16, wherein the guide includes a bore disposed therein that slidably receives the rod therethrough.

* * * * *

UNITED STATES PATENT AND TRADEMARK OFFICE
CERTIFICATE OF CORRECTION

PATENT NO. : 10,064,742 B2
APPLICATION NO. : 15/487791
DATED : September 4, 2018
INVENTOR(S) : Taylor et al.

Page 1 of 1

It is certified that error appears in the above-identified patent and that said Letters Patent is hereby corrected as shown below:

In the Claims

In Column 24, Line 4, in Claim 10, delete "a a" and insert --a-- therefor

In Column 24, Line 29, in Claim 10, after "to", delete "a"

Signed and Sealed this
Twenty-sixth Day of March, 2019

Andrei Iancu
*Director of the United States Patent and Trademark Office*